US011833159B2

(12) United States Patent
McCall et al.

(10) Patent No.: US 11,833,159 B2
(45) Date of Patent: *Dec. 5, 2023

(54) NON-HORMONAL STEROID MODULATORS OF NF-KB FOR TREATMENT OF DISEASE

(71) Applicant: ReveraGen BioPharma, Inc., Rockville, MD (US)

(72) Inventors: John M. McCall, Boca Grande, FL (US); Eric Hoffman, Rockville, MD (US); Kanneboyina Nagaraju, Highland, MD (US)

(73) Assignee: ReveraGen BioPharma, Inc., Rockville, MD (US)

( * ) Notice: Subject to any disclaimer, the term of this patent is extended or adjusted under 35 U.S.C. 154(b) by 367 days.

This patent is subject to a terminal disclaimer.

(21) Appl. No.: 17/082,521

(22) Filed: Oct. 28, 2020

(65) Prior Publication Data

US 2021/0052606 A1 Feb. 25, 2021

Related U.S. Application Data

(60) Continuation of application No. 16/226,061, filed on Dec. 19, 2018, now Pat. No. 10,857,161, which is a continuation of application No. 15/483,863, filed on Apr. 10, 2017, now Pat. No. 10,206,933, which is a division of application No. 15/229,947, filed on Aug. 5, 2016, now Pat. No. 9,649,320, which is a continuation of application No. 14/164,779, filed on Jan. 27, 2014, now Pat. No. 9,434,758, which is a division of application No. 13/678,253, filed on Nov. 15, 2012, now Pat. No. 8,673,887, which is a division of application No. 13/327,628, filed on Dec. 15, 2011, now Pat. No. 8,334,279, which is a division of application No. 12/473,921, filed on May 28, 2009, now Pat. No. 8,207,151.

(60) Provisional application No. 61/056,715, filed on May 28, 2008.

(51) Int. Cl.
| A61K 31/573 | (2006.01) |
| A61K 31/575 | (2006.01) |
| C07J 5/00 | (2006.01) |
| A61K 31/57 | (2006.01) |
| A61P 1/04 | (2006.01) |
| A61P 1/16 | (2006.01) |
| A61P 3/00 | (2006.01) |

(52) U.S. Cl.
CPC .......... *A61K 31/573* (2013.01); *A61K 31/57* (2013.01); *A61K 31/575* (2013.01); *A61P 1/04* (2018.01); *A61P 1/16* (2018.01); *A61P 3/00* (2018.01); *C07J 5/0038* (2013.01); *C07J 5/0053* (2013.01); *C07J 5/0076* (2013.01); *Y02A 50/30* (2018.01)

(58) Field of Classification Search
CPC ....... A61K 31/573; A61K 31/58; A61P 19/02; A61P 29/00; A61P 3/00; A61P 3/10; C07J 7/003

See application file for complete search history.

(56) References Cited

U.S. PATENT DOCUMENTS

| 2,776,927 A | 1/1957 | Shull |
| 2,838,536 A | 6/1958 | Magerklein |
| 2,894,963 A | 7/1959 | Gould |
| 2,957,893 A | 10/1960 | Herzog |
| 2,980,713 A | 4/1961 | Chemerda |
| 3,004,965 A | 10/1961 | Kerwin |
| 3,009,933 A | 11/1961 | Robinson |
| 3,047,468 A | 7/1962 | Origoni |
| 3,053,866 A | 9/1962 | Chemerda |
| 3,087,938 A | 4/1963 | Reimann |
| 3,098,086 A | 7/1963 | Albert |
| 3,127,425 A | 3/1964 | Reimann |
| 3,284,477 A | 11/1966 | Rausser |
| 3,463,852 A | 8/1969 | Reimann |
| 3,681,405 A | 8/1972 | Laurent |
| 3,842,105 A | 10/1974 | Helmut |
| 3,891,631 A | 6/1975 | Phillipps |
| 3,923,985 A | 12/1975 | Marechal |
| 4,041,055 A | 8/1977 | Shephard |
| 4,076,708 A | 2/1978 | Green |
| 4,260,464 A | 4/1981 | Kerb |
| 4,318,853 A | 3/1982 | Ayer |
| 4,336,200 A | 6/1982 | Ayer |
| 4,404,141 A | 9/1983 | Annen |
| 4,427,591 A | 1/1984 | Ayer |
| 4,444,689 A | 4/1984 | Ayer |
| 4,472,393 A | 9/1984 | Shapiro |

(Continued)

FOREIGN PATENT DOCUMENTS

| CA | 975755 A | 10/1975 |
| CA | 983919 A | 2/1976 |

(Continued)

OTHER PUBLICATIONS

"Heart Failure: Understanding Heart Failure." Cleveland Clinic website. https://my.clevelandclinic.org/health/diseases/17069-heart-failure-understanding-heart-failure. Published Dec. 18, 2017.

(Continued)

*Primary Examiner* — Savitha M Rao
(74) *Attorney, Agent, or Firm* — Cynthia Hathaway; Lauren L. Stevens; Erik M. Larsen

(57) ABSTRACT

The present invention relates to compounds and methods which may be useful as treatments of neuromuscular diseases such as muscular dystrophy, and as inhibitors of NF-κB for the treatment or prevention of muscular wasting disease, including muscular dystrophy.

12 Claims, No Drawings

(56) References Cited

U.S. PATENT DOCUMENTS

| | | |
|---|---|---|
| 4,555,507 A | 11/1985 | Annen |
| 4,613,463 A | 9/1986 | Sacks |
| 4,645,763 A | 2/1987 | Annen |
| 4,701,451 A | 10/1987 | Annen |
| 4,771,042 A | 9/1988 | Braughler |
| 4,777,165 A | 10/1988 | Annen |
| 4,876,250 A | 10/1989 | Clark |
| 4,891,426 A | 1/1990 | Vanrheenen |
| 4,910,192 A | 3/1990 | Avery |
| 4,920,216 A | 4/1990 | Breslow |
| 4,929,395 A | 5/1990 | Vanrheenen |
| 4,948,533 A | 8/1990 | Braughler |
| 4,975,536 A | 12/1990 | Shephard |
| 4,975,537 A | 12/1990 | Aristoff |
| 4,977,255 A | 12/1990 | Livingston |
| 4,990,612 A | 2/1991 | Vanrheenen |
| 4,994,443 A | 2/1991 | Folkman |
| 5,001,116 A | 3/1991 | Folkman |
| 5,225,335 A | 7/1993 | Kominek |
| 5,248,773 A | 9/1993 | Boivin |
| 5,310,896 A | 5/1994 | Devocelle |
| 5,412,091 A | 5/1995 | Boivin |
| 5,434,258 A | 7/1995 | Devocelle |
| 5,451,690 A | 9/1995 | Devocelle |
| 5,502,183 A | 3/1996 | Andrews |
| 5,502,222 A | 3/1996 | Fu |
| 5,508,452 A | 4/1996 | Roussel |
| 5,616,742 A | 4/1997 | Fu |
| 5,616,743 A | 4/1997 | Boivin |
| 5,731,447 A | 3/1998 | Buendia |
| 5,750,745 A | 5/1998 | Fu |
| 5,939,302 A | 8/1999 | Goeddel |
| 5,972,922 A | 10/1999 | Wilks |
| 5,990,099 A | 11/1999 | Clark |
| 6,011,012 A | 1/2000 | Ni |
| 6,011,023 A | 1/2000 | Clark |
| 6,030,834 A | 2/2000 | Chu |
| 6,090,794 A | 7/2000 | Martuza |
| 6,090,798 A | 7/2000 | Clark |
| 6,169,178 B1 | 1/2001 | La Loggia |
| 6,194,565 B1 | 2/2001 | Buendia |
| 6,500,814 B1 | 12/2002 | Hesch |
| 8,207,151 B2 | 6/2012 | McCall |
| 8,334,279 B2 | 12/2012 | McCall |
| 8,673,887 B2 | 3/2014 | McCall |
| 9,198,921 B2 | 12/2015 | McCall |
| 9,434,758 B2 | 9/2016 | McCall |
| 9,649,320 B2 | 5/2017 | McCall |
| 10,206,933 B2 | 2/2019 | McCall |
| 10,464,967 B2 | 11/2019 | McCall |
| 10,799,514 B2 | 10/2020 | McCall |
| 10,857,161 B2 | 12/2020 | McCall |
| 11,382,922 B2 | 7/2022 | McCall |
| 11,471,471 B2 | 10/2022 | McCall |
| 2002/0002155 A1 | 1/2002 | Bhatnagar |
| 2003/0032630 A1 | 2/2003 | Merlos Roca |
| 2004/0181055 A1 | 9/2004 | Murillo Garrido |
| 2005/0090553 A1 | 4/2005 | Shapiro |
| 2006/0018933 A1 | 1/2006 | Vaya |
| 2006/0024365 A1 | 2/2006 | Vaya |
| 2006/0025436 A1 | 2/2006 | Ridgway |
| 2006/0089395 A1 | 4/2006 | Muto |
| 2006/0153916 A1 | 7/2006 | Vaya |
| 2007/0212751 A1 | 9/2007 | Messinger |
| 2007/0225315 A1 | 9/2007 | Guttridge |
| 2008/0064753 A1 | 3/2008 | Palladino |
| 2008/0090791 A1 | 4/2008 | Reading |
| 2008/0234380 A1 | 9/2008 | Shapiro |
| 2009/0099191 A1 | 4/2009 | Gudkov |
| 2010/0087408 A1 | 4/2010 | McCall |
| 2014/0018337 A1 | 1/2014 | Frincke |
| 2015/0011519 A1 | 1/2015 | McCall |
| 2019/0125763 A1 | 5/2019 | McCall |
| 2020/0148717 A1 | 5/2020 | McCall |
| 2020/0281942 A1 | 9/2020 | McCall |
| 2021/0046089 A1 | 2/2021 | McCall |
| 2022/0324902 A1 | 10/2022 | McCall |
| 2023/0027370 A1 | 1/2023 | McCall |

FOREIGN PATENT DOCUMENTS

| | | |
|---|---|---|
| CA | 1086715 A | 9/1980 |
| CA | 2725008 | 12/2009 |
| CN | 1896090 A | 1/2007 |
| CN | 1907999 A | 2/2007 |
| CN | 101412742 A | 10/2007 |
| CN | 101347438 A | 1/2009 |
| CN | 101353368 A | 1/2009 |
| CN | 101397319 A | 4/2009 |
| CN | 101397320 A | 4/2009 |
| CN | 101434631 A | 5/2009 |
| CN | 101624414 A | 1/2010 |
| CN | 101759742 | 6/2010 |
| DE | 3149475 A1 | 7/1982 |
| DE | 3227312 A1 | 1/1984 |
| EP | 0057401 A1 | 8/1982 |
| EP | 0097328 A2 | 1/1984 |
| EP | 0114589 A1 | 8/1984 |
| EP | 0126877 A1 | 12/1984 |
| EP | 0156643 A2 | 10/1985 |
| EP | 0164298 A2 | 12/1985 |
| EP | 0263213 A1 | 4/1988 |
| EP | 0875516 A2 | 11/1998 |
| EP | 1236469 | 9/2002 |
| EP | 1236469 A2 | 9/2002 |
| EP | 1336602 A1 | 8/2003 |
| ES | 0445981 A1 | 6/1977 |
| FR | 1433301 | 6/1959 |
| FR | 335 M | 3/1961 |
| GB | 814000 A | 5/1959 |
| GB | 843214 A | 8/1960 |
| GB | 843215 A | 8/1960 |
| GB | 901093 A | 7/1962 |
| GB | 912378 A | 12/1962 |
| GB | 928301 A | 6/1963 |
| GB | 928302 A | 6/1963 |
| GB | 959378 A | 6/1964 |
| GB | 1115893 | 5/1968 |
| GB | 1480763 | 7/1977 |
| GB | 1480763 A | 7/1977 |
| GB | 2089808 A | 6/1982 |
| GB | 2131811 | 6/1984 |
| GB | 2131811 A | 6/1984 |
| JP | H04504572 A | 8/1992 |
| JP | H05500054 A | 1/1993 |
| JP | H05507912 A | 11/1993 |
| JP | 2003081836 | 3/2003 |
| JP | 2009126852 | 6/2009 |
| JP | 5780521 B | 9/2015 |
| RU | 2156256 C1 | 9/2000 |
| WO | 1987001706 | 3/1987 |
| WO | 1987007895 | 12/1987 |
| WO | 1988007092 | 9/1988 |
| WO | 1988007527 | 10/1988 |
| WO | 1988009337 | 12/1988 |
| WO | 1990012577 | 11/1990 |
| WO | 1990015816 | 12/1990 |
| WO | 1991019731 | 12/1991 |
| WO | 1993025570 | 12/1993 |
| WO | 1995018621 | 7/1995 |
| WO | 1996006618 | 3/1996 |
| WO | 1996010402 | 4/1996 |
| WO | 1997022616 | 6/1997 |
| WO | 1997039018 | 10/1997 |
| WO | 1999003503 | 1/1999 |
| WO | 1999017778 | 4/1999 |
| WO | 1999032102 | 7/1999 |
| WO | 1999061030 | 12/1999 |
| WO | 2000038653 | 7/2000 |
| WO | 2002000001 | 1/2002 |
| WO | 2002043785 | 6/2002 |
| WO | 2003014141 | 2/2003 |
| WO | 2004012699 | 2/2004 |
| WO | 2006007910 | 1/2006 |

(56) References Cited

FOREIGN PATENT DOCUMENTS

| WO | 2007016979 | 2/2007 |
|---|---|---|
| WO | 2009155056 | 12/2009 |
| WO | 2010041827 | 4/2010 |
| WO | 2011127048 | 10/2011 |
| WO | 2013082253 | 6/2013 |
| WO | 2017004205 | 1/2017 |

OTHER PUBLICATIONS

Agusti, A., "Systemic Effects of Chronic Obstructive Pulmonary Disease: What We Know and What We Don't Know (But Should)", Proc Am Thorac Soc., 4(7):522-5, (2007).
Asahara, H. et al., "High DNA-Binding Activity of Transcription Factor NF-kappa B in Synovial Membranes of Patients with Rheumatoid Arthritis", Biochem Mol Biol Int., 37(5):827-32, (1995).
Atreya, I. et al., "NF-KB in Inflammatory Bowel Disease", J Inter Med., 263(6):591-6, (2008).
Baeuerle, P. et al., "NF-kB: Ten Years After", Cell, 87(1):13-20, (1996).
Bao, Z. et al., "A Novel Antiinflammatory Role for Andrographolide in Asthma via Inhibition of the Nuclear Factor-kappa B Pathway," Am J Respir Crit Care Med., 179(8):657-65, (2009).
Barnes, P., "The Cytokine Network in Asthma and Chronic Obstructive Pulmonary Disease", J Clin Invest., 118(11):3546-56, (2008).
Bikdeli, B. et al., Two Decades of Cardiovascular Trials With Primal Surrogate Endpoints: 1990-2011, J Am Heart Assoc. 2017; 6:e005285, pp. 1-9.
De Groote, P. et al., "Long-Term Functional and Clinical Follow-Up of Patients With Heart Failure With Recovered Left Ventricular Ejection Fraction After β-Blocker Therapy", Circ. Heart Fail., Downloaded from http://ahajournals.org on Dec. 3, 2018; pp. 434-439, (2014).
Declaration under 37 C.F.R. § 1.132 of John M. McCall, Ph D., dated Feb. 12, 2018; 17 pages.
Definition of "Glioma", American Brain Tumor Association (ABTA), online at http://www.abta.org/brain-tumor-informationtypes-=of-tumors/glioma.html?print=t; accessed Mar. 9, 2016; 3 pages; (2016).
Del Prete, A. et al., "Molecular Pathways in Cancer-Related Inflammation", Biochem Med (Zagreb)., 21(3):264-75, (2011).
Di Meglio, P. et al., "Amelioration of Acute Inflammation by Systemic Administration of a Cell-Permeable Peptide Inhibitor of NF-kB Activation", Arthritis Rheum., 52(3):951-8, (2005).
Di Stefano, A. et al., "Increased Expression of Nuclear Factor-KB in Bronchial Biopsies From Smokers and Patients with COPD", Eur Respir J., 20(3):556-63, (2002).
Edwards, M. et al., "Targeting the NF-κB Pathway in Asthma and Chronic Obstructive Pulmonary Disease", Pharmacol Ther., 121(1):1-13, (2009).
EP Application No. 09767367.7; European Extended Search Report, dated May 12, 2011; 11 pages.
EP Patent Application No. 12853185.2; Extended European Search Report, dated Apr. 28, 2015; 12 pages.
Freishtat, R. et al., "Beneficial Glucocorticoid Effects in Asthmatic Airway Epithelium Are Not Dependent On Receptor-Mediated Transcription", Am Fed Med Res., 1 page, (Apr. 2001).
Fukuma, K. et al., "Effect of Lazaroid U-74389G and Methyl prednisolone On Endotoxin-Induced Shock In Mice," Surgery, 125(4):421-30, (1999).
Gong, H. et al., "Dexamethasone Rapidly Inhibits Glucose Uptake via Non-Genomic Mechanisms in Contracting Myotubes", Arch Biochem Biophys., 603:102-9, (2016).
GPG1004 Report and Results, Source: Patent Information Services, Inc. Online Patent and Literature Searching, 113 pages; Apr. 12, 2010.
GPG1017 Report and Results, Source: Patent Information Services, Inc. Online Patent and Literature Searching, 171 pages; Jan. 23, 2011.

GPG903 Report and Results, Source: Patent Information Services, Inc. Online Patent And Literature Searching, 22 pages; Apr. 22, 2009.
GPG903A Report and Results, Source: Patent Information Services, Inc. Online Patent and Literature Searching, 385 pages; Apr. 22, 2009.
Gulati, G. et al., "Heart Failure With Improved Ejection Fraction: Is it Possible to Escape One's Past?", JACC: Heart Failure, 6(9):725-33, (2018).
Hall, E. et al., "Effects of the 21-Aminosteroid U74006F on Experimental Head Injury in Mice", J Neurosurg., 68(3):456-61, (1988).
Heier, C. et al., "Vamorolone Targets Dual Nuclear Receptors to Treat Inflammation and Dystrophic Cardiomyopathy", Life Science Alliance, 2(1):e201800186, (2019).
Heier, C. et al., "VBP15, A Novel Anti-Inflammatory and Membrane-Stabilizer, Improves Muscle Dystrophy Without Side Effects", EMBO Mol Med, 5(10):1569-85, (2013).
Hori, Y. et al., "Differential Effects of Angiostatic Steroids and Dexamethasone on Angiogenesis and Cytokine Levels in Rat Sponge Implants", Br J Pharmacol., 118(7):1584-91, (1996).
International Application No. PCT/US2009/045489; International Preliminary Report on Patentability, date of issuance Nov. 30, 2010; 7 pages.
International Application No. PCT/US2009/045489; International Search Report and Written Opinion of the International Searching Authority, dated Jan. 29, 2010; 11 pages.
International Application No. PCT/US2012/067003; Declaration of Non-Establishment of International Search Report and Written Opinion of the International Searching Authority, dated Feb. 25, 2013; 4 pages.
International Application No. PCT/US2012/067003; International Preliminary Report on Patentability, date of issuance Jun. 3, 2014; 4 pages.
International Application No. PCT/US2016/040098; International Preliminary Report on Patentability, date of issuance Jan. 2, 2018; 4 pages.
International Application No. PCT/US2016/040098; International Search Report and Written Opinion of the International Search Authority, dated Sep. 15, 2016; 5 pages.
Izmailova, E. et al., "Use of Molecular Imaging to Quantify Response to IKK-2 Inhibitor Treatment in Murine Arthritis", Arthritis Rheum., 56(1):117-28, (2007).
Jacobsen, J. et al., "Novel 21-Aminosteroids That Inhibit Iron-Dependent Lipid Peroxidation and Protect Against Central Nervous System Trauma", J Med Chem., 33(4):1145-51, (1990).
Jobin, C. et al., "NF-kB Signaling Proteins as Therapeutic Targets for Inflammatory Bowel Diseases", Inflamm Bowel Dis., 6(3):206-13, (2000).
Johnson, J. et al., "Relationships Between Drug Activity and NCI Preclinical In Vitro and In Vivo Models and Early Clinical Trials", Br J Cancer, 84(10):1424-31, (2001).
Kalsi, J. et al., "Suppressive Effects of a Novel Antioxidant Compound on Human T Cell Functions In Vitro", Agents Actions, (Special Conference Issue), 39(Suppl1):C110-C112, (1993).
Kaltschmidt, B. et al., "Activation of NF-κB by Reactive Oxygen Intermediates in the Nervous System", Antioxid Redox Signal., 1(2):129-44, (1999).
Lawrence, T., "The Nuclear Factor NF-kappaB Pathway in Inflammation", Cold Spring Harb Perspect Biol., 1(6):a001651, (2009).
Lin, Y. et al., "Dexamethasone Reduced Invasiveness of Human Malignant Glioblastoma Cells Through a MAPK Phosphatase-1 (MKP-1) Dependent Mechanism", Eur J Pharmacol., 593(1-3):1-9, (2008).
Lindner, V., "The NF-kappaB and IkappaB System in Injured Arteries", Pathobiol., 66(6):311-20, (1998).
Loprizi, C. et al., "Randomized Comparison of Megestrol Acetate versus Dexamethasone versus Fluoxymesterone for the Treatment of Cancer Anorexia/Cachexia", J Clin Oncol., 17(10):3299-306, (1999).
Louis, D., "Molecular Pathology of Malignant Gliomas", Annu Rev Pathol., 1:97-117, (2006).

(56) References Cited

OTHER PUBLICATIONS

Lührs, H. et al., "Butyrate Inhibits NF-κB Activation in Lamina Propria Macrophages of Patients with Ulcerative Colitis", Scand J Gastroenterol., 37(4):458-66, (2002).
Lupón, J. et al., "Recovered Heart Failure With Reduced Ejection Fraction and Outcomes: A Prospective Study", European Journal of Heart Failure, 19:1615-23, (2017).
Maeda, S. et al., "Nod2 Mutation in Crohn's Disease Potentiates NF-κB Activity and IL-1β Processing", Science, 307(57):734-8, (2005).
McGuire, C. et al., "Nuclear Factor Kappa B (NF-.kappa.B) in Multiple Sclerosis Pathology", Trends Mol Med., 19(10):604-13, (2013).
McNatt, L. et al., "Angiostatic Activity of Steroids in the Chick Embryo CAM and Rabbit Cornea Models of Neovascularization", J Ocul Pharmacol Ther., 15(5):413-23, (1999).
Metzinger, L. et al., "Lazaroids Enhance Skeletal Myogenesis in Primary Cultures of Dystrophin-Deficient Mdx Mice", J Neurol Sci., 126(2):138-45, (1994).
Metzinger, L. et al., "Modulation by Prednisolone of Calcium Handling in Skeletal Muscle Cells", Br J Pharmacol., 116(7):2811-6, (1995).
Nadruz, W. et al., "Heart Failure and Midrange Ejection Fraction: Implications of Recovered Ejection Fraction for Exercise Tolerance and Outcomes", Downloaded from http://ahajournals.org on Dec. 3, 2018; pp. 1-8, (2016).
Niazi, S., "Handbook of Pharmaceutical Manufacturing Formulations: Sterile Products", CRC Press LLC, Preface to the Series, 1 page, (2004).
Onai Y et al., Inhibition of NF-κB improves left ventricular remodeling and cardiac dysfunction after myocardial infarction, Am J Physiol Heart Circ Physiol. Jan. 2007;292(1):H530-H538.
Park, J. et al., "Recurrence of Left Ventricular Dysfunction in Patients With Restored Idiopathic Dilated Cardiomyopathy", Clin Cardiol., 37(4):222-6, (2014).
Peterson, J. et al., "Peptide-Based Inhibitioon of NF-KB Rescues Diaphragm Muscle Contractile Dysfunction in a Murine Model of Duchenne Muscular Dystrophy", Mol Med., 17(5-6):508-15, (2011).
Poynter, M. et al., "NF-kB activation in Airways Modulates Allergic Inflammation but Not Hyperresponsiveness", J Immunol., 173(11):7003-9, (2004).
Pubchem-'668'. Create Date: Aug. 8, 2005 (Aug. 8, 2005) Date Accessed: Aug. 18, 2016 (Aug. 18, 2016); p. 3, compound.
Puliyappadamba, V. et al., "The Role of NF-kappaB in the Pathogenesis of Glioma", Mol Cell Oncol., 1(3):e963478, (2014).
Raychaudhuri, B. et al., "Aberrant Constitutive Activation of Nuclear Factor KB in Glioblastoma Multiforme Drives Invasive Phenotype", J Neurooncol., 85(1):39-47, (2007).
Reeves, E. et al., "VBP15: Preclinical Characterization of a Novel Anti-inflammatory Delta 9, 11 Steroid", Bioorg Med Chem., 21(8):2241-9, (2013).
Ridder, D. et al., "NF-kappaB Signaling in Cerebral Ischemia", Neuroscience, 158(3):995-1006, (2009).
SciFinder search results, (May 28, 2009), 1-20.
Tak, P. et al., "NF-κB: A Key Role in Inflammatory Diseases", J Clin Invest., 107(1):7-11, (2001).
Teramoto, S. et al., "The Role of Nuclear Factor-κB Activation in Airway Inflammation Following Adenovirus Infection and COPD", Chest, 119(4):1294-5, (2001).
U.S. Appl. No. 12/473,921; Notice of Allowance, dated Jan. 20, 2012; 10 pages.
U.S. Appl. No. 12/473,921; Notice of Allowance, dated May 15, 2012; 8 pages.
U.S. Appl. No. 13/327,628; Notice of Allowance, dated Aug. 17, 2012; 9 pages.
U.S. Appl. No. 13/678,253; Examiner-Initiated Interview Summary, dated Oct. 25, 2013; 1 page.
U.S. Appl. No. 13/678,253; Notice of Allowance, dated Oct. 25, 2013; 12 pages.
U.S. Appl. No. 14/164,779; Notice of Allowance, dated May 5, 2016; 8 pages.
U.S. Appl. No. 14/360,384; Final Office Action, dated Aug. 11, 2017; 16 pages.
U.S. Appl. No. 14/360,384; Final Office Action, dated Mar. 11, 2019; 25 pages.
U.S. Appl. No. 14/360,384; Non-Final Office Action, dated May 18, 2018; 19 pages.
U.S. Appl. No. 14/360,384; Non-Final Office Action, dated Oct. 18, 2016; 15 pages.
U.S. Appl. No. 14/360,384; Notice of Allowability, dated Sep. 25, 2019; 6 pages.
U.S. Appl. No. 14/360,384; Notice of Allowance, dated Jun. 24, 2019; 8 pages.
U.S. Appl. No. 14/360,384; Response After Final Office Action, dated Feb. 12, 2018; 12 pages.
U.S. Appl. No. 14/360,384; Response to Non-Final Office Action, dated Apr. 18, 2017; 6 pages.
U.S. Appl. No. 14/360,384; Response to Restriction Requirement, dated Jul. 26, 2016; 5 pages.
U.S. Appl. No. 15/197,118 ; Examiner-Initiated Interview Summary, dated May 20, 2020; 3 pages.
U.S. Appl. No. 15/197,118; Advisory Action, dated Nov. 27, 2017; 3 pages.
U.S. Appl. No. 15/197,118; Applicant-Initiated Interview Summary, dated Dec. 14, 2018; 3 pages.
U.S. Appl. No. 15/197,118; Final Office Action, dated Aug. 17, 2017; 7 pages.
U.S. Appl. No. 15/197, 118; Final Office Action, dated Oct. 30, 2018; 14 pages.
U.S. Appl. No. 15/197,118; Non-Final Office Action, dated Apr. 4, 2017; 9 pages.
U.S. Appl. No. 15/197, 118; Non-Final Office Action, dated Mar. 22, 2018; 14 pages.
U.S. Appl. No. 15/197,118; Patent Board Decision—Examiner Reversed, dated Feb. 26, 2020; 1 page.
U.S. Appl. No. 15/197,118; Response to Final Office Action, dated Nov. 16, 2017; 8 pages.
U.S. Appl. No. 15/197,118; Response to Non-Final Office Action, dated Aug. 4, 2017; 8 pages.
U.S. Appl. No. 15/229,947; Examiner-Initiated Interview Summary, dated Jan. 10, 2017; 1 page.
U.S. Appl. No. 15/229,947; Notice of Allowance, dated Jan. 10, 2017; 10 pages.
U.S. Appl. No. 15/483,863; Amendment and Response to Non-Final Office Action, dated Jun. 4, 2018; 8 pages.
U.S. Appl. No. 15/483,863; Applicant-Initiated Interview Summary, dated Oct. 3, 2018; 1 page.
U.S. Appl. No. 15/483,863; Final Office Action, dated Aug. 10, 2018; 21 pages.
U.S. Appl. No. 15/483,863; Non-Final Office Action, dated Mar. 5, 2018; 17 pages.
U.S. Appl. No. 15/483,863; Notice of Allowance, dated Oct. 3, 2018; 13 pages.
U.S. Appl. No. 16/580,883; Non-Final Office Action, dated Oct. 5, 2020; 37 pages.
U.S. Appl. No. 17/008,237; Application as filed, dated Aug. 31, 2020; 86 pages.
Vernier, A. et al., "Antioxidant Lazaroids Enhance Differentiation of C2 Skeletal Muscle Cells", Neurosci Lett., 186(2-3):177-80, (1995).
Voelkel, N. et al., "Pulmonary Vascular Involvement in Chronic Obstructive Pulmonary Disease", Eur Respir J Supp., 22(46):28-32, (2003).
Voskoglou-Nomikos, T. et al., "Clinical Predictive Value of the in Vitro Cell Line, Human Xenograft, and Mouse Allograft Preclinical Cancer Models", Clin Cancer Res., 9(11):4227-39, (2003).
Weinstein, R. et al., "Promotion of Osteoclast Survival and Antagonism of Bisphosphonate-Induced Osteoclast Apoptosis by Glucocorticoids", J Clin Invest., 109(8):1041-8, (2002).
Weintraub, W. et al., "The Perils of Surrogate Endpoints", Eur Heart J., 36(33):2212-8, (2015).
Wells, E. et al., "Vamorolone, a Dissociative Steroidal Compound, Reduced Pro-Inflammatory Cytokine Expression in Glioma Cells

(56) References Cited

OTHER PUBLICATIONS and Increase Activity and Survival in Murine Model of Cortical Tumor", Oncotarget, 8(6):9366-74, (2017).
Yan, J. et al., "NF-κB, A Potential Therapeutic Target For the Treatment of Multiple Sclerosis", CNS Neurol Disord Drug Targets, 7(6):536-57, (2008).
Yang, C. et al., "Immunolocalization of Transcription Factor NF-kappa B in Inclusion-Body Myositis Muscle and at Normal Human Neuromuscular Junctions", Neurosci Lett., 254(2):77-80, (1998).
Zhong, J. et al., "Regulation of Oxygen Free Radical on Expression of Interleukin-8 in Gastric Cancer Cell Line SGC-7901", Zhongguo Zongxiyi Jiehe Waike Zazhi, 12(3):264-8, (2006), Abstract.
"Duchenne Muscular Dystrophy and Related Dystrophinopathies: Developing Drugs for Treatment Guidance for Industry", FDA Guidance Document issued by the Center for Drug Evaluation and Research, published Feb. 2018; 16 pages.
Fiorillo, A. et al., "Muscle miRNAome Shows Suppression of Chronic InflammatorymiRNAs with Both Prednisone and Vamorolone", Physiol Genomics, 50(9):735-745, (2018).
Fiorillo, A. et al., "TNFα-induced MicroRNAs Control Dystrophin Expression in Becker Muscular Dystrophy", Cell Rep., 12(10): 27 pages, (2015).
Kinder, T. et al., "Muscle Weakness in Myositis: MicroRNA-Mediated Dystrophin Reduction in a Myositis Mouse Model and Human Muscle Biopsies", Arthritis & Rheumatology, 72(7): 1170-1183, (2020).
Liu, X. et al., "Disruption of a key ligand-H-bond network drives dissociative properties in vamorolone for Duchenne muscular dystrophy treatment", Proc. Natl. Acad. Sci. U.S.A., 117(39):24285-93, (2020).
Matthews, E. et al., "Corticosteroids for the treatment of Duchenne muscular dystrophy", Cochrane Database Syst. Rev., 5, (2016), 116 pages.
Mavroudis, P. et al., "Population Pharmacokinetics of Vamorolone (VBP15) in Healthy Men and Boys With Duchenne Muscular Dystrophy", J Clin Pharmacol. 59(7):979-88, (2019).
McDonald, C. et al., "Long-term effects of glucocorticoids on function, quality of life, and survival in patients with Duchenne muscular dystrophy: a prospective cohort study", Lancet, 391(10119):451-61, (2018).
Smith, E. et al., "Efficacy and safety of vamorolone in Duchenne muscular dystrophy: An 18-month interim analysis of a non-randomized open-label extension study", PLOS Med., 17(9): e1003222, (2020).
Ward, L., "Glucocorticoid-Induced Osteoporosis: Why Kids Are Different", Front Endocrinol (Lausanne), 11:576, (2020).
Xiao, L. et al., "New Paradigms in Inflammatory Signaling in Vascular Endothelial Cells", Am J Physiol Heart Circ Physiol, 306:H317-H325, (2014).
Roy, R. et al., "Acute Serum Protein and Cytokine Response of Single Dose of Prednisone in Adult Volunteers", Steroids, 178(2):108953, 9 pages, (2022).
Smith, E. et al., "Vamorolone Newsletter #1", ReverGen BioPharma, 1(1):1-6, (2017).
Sreetama, S. et al., "Membrane Stabilization by Modified Steroid Offers a Potential Therapy for Muscular Dystrophy Due to Dysferlin Deficit", Molecular Therapy, 26(9):2231-2242, (2018).
Takeda, S. et al., "Exon-Skipping in Duchenne Muscular Dystrophy", Journal of Neuromuscular Diseases, 8:S343-S358, (2021).
U.S. Appl. No. 12/473,921.
U.S. Appl. No. 13/327,628.
U.S. Appl. No. 15/197,118; Notice of Allowance, dated Jun. 4, 2020; 22 pages.
U.S. Appl. No. 16/226,061; Non-Final Office Action, dated Feb. 5, 2020; 26 pages.
U.S. Appl. No. 16/811,973; Notice of Allowability, dated May 18, 2022; 4 pages.
U.S. Appl. No. 16/811,973; Notice of Allowance, dated Mar. 10, 2022; 33 pages.
U.S. Appl. No. 16/811,973; Notice of Allowance, dated May 4, 2022; 15 pages.
U.S. Appl. No. 17/008,237; Non-Final Office Action, dated Aug. 5, 2022; 18 pages.
U.S. Appl. No. 17/008,237; Notice of Allowance, dated Feb. 9, 2023; 12 pages.
U.S. Appl. No. 17/651,877; Notice of Allowance, dated May 19, 2022; 23 pages.
Ward, L. et al., "Proceedings of a Parent Project Muscular Dystrophy Bone Health Workshop: Morbidity due to osteoporosis in DMD: The Path Forward May 12-13, 2016, Bethesda, Maryland, USA", Neuromuscular Disorders, 28(1):64-76, (2018).
Ziemba, M. et al., "Biomarker-Focused Multi-Drug Combination Therapy and Repurposing Trial in MDX Mice", PloS One, 16(2):e0246507, 19 pages, (2021).
"A Study to Assess the Efficacy and Safety of Vamorolone in Boys With Duchenne Muscular Dystrophy (DMD)", ClinicalTrials.gov Identifier: NCT03439670, 16 pages, (first posted: Feb. 20, 2018).
"A Study to Assess Vamorolone in Becker Muscular Dystrophy (BMD)", ClinicalTrials.gov Identifier: NCT05166109, 13 pages, (first posted: Dec. 21, 2021).
"A Study to Assess Vamorolone in Boys Ages 2 to <4 Years and 7 to <18 Years With Duchenne Muscular Dystrophy (DMD)", ClinicalTrials.gov Identifier: NCT05185622, 16 pages, (first posted: Jan. 11, 2022).
"A Study to Assess Vamorolone in Boys With Duchenne Muscular Dystrophy (DMD)", ClinicalTrials.gov Identifier: NCT02760264, 12 pages, (first posted: May 3, 2016).
"An Extension Study to Assess Vamorolone in Boys With Duchenne Muscular Dystrophy (DMD)", ClinicalTrials.gov Identifier: NCT02760277, 12 pages, (first posted: May 3, 2016).
"Expanded Access Protocol for Boys With Duchenne Muscular Dystrophy", ClinicalTrials.gov Identifier: NCT03863119, 6 pages, (first posted: Mar. 5, 2019).
"Long-term Extension Study to Assess Vamorolone in Boys With Duchenne Muscular Dystrophy (DMD)", ClinicalTrials.gov Identifier: NCT03038399, 9 pages, (first posted: Jan. 31, 2017).
"Proof of Concept Trial of Vamorolone in Pediatric Ulcerative Colitis", ClinicalTrials.gov Identifier: NCT04348890, 7 pages, (first posted: Apr. 16, 2020).
Aartsma-Rus, A. et al., "226th ENMC International Workshop: Towards validated and qualified biomarkers for therapy development for Duchenne muscular dystrophy Jan. 20-22, 2017, Heemskerk, The Netherlands", Neuromuscul. Disord., 28(1):77-86, (2018).
Benny Klimek, M. et al., "Effects of Chronic, Maximal Phosphorodiamidate Morpholino Oligomer (PMO) Dosing on Muscle Function and Dystrophin Restoration in a Mouse Model of Duchenne Muscular Dystrophy", J. of Neuromuscul. Dis. Preprint: 1-13, (2021).
Clemens, P. et al., "P.337Dystrophin Restoration by Exon 53 Skipping in Patients with Duchenne Muscular Dystrophy After Viltolarsen Treatment: Phase 2 Study Update", Neuromuscl. Disord., 29(1):S165-S166, Abstract, (2019).
Clemens, P. et al., "P.338Vamorolone Trial in Duchenne Muscular Dystrophy Shows Dose-Related Improvement of Muscle Function", Neuromuscul. Dis., 29(1):S166, Abstract, (2019).
Clemens, P. et al., "Drug Development of Vamorolone for Duchenne Muscular Dystrophy", Neuromuscul. Disord., 27(2):S217-S218, (2017).
Conklin, L. et al., "Developmental Pharmacodynamics and Modeling in Pediatric Drug Development", J. Clin. Pharmacol., 59(1):S87-S94, (2019).
Conklin, L. et al., "Phase IIa Trial in Duchenne Muscular Dystrophy Shows Vamorolone is a First-in-Class Dissociative Steroidal Anti-Inflammatory Drug", Pharmacol. Res., 136:140-150, (2018).
Conklin, L. et al., "Serum Biomarkers of Glucocorticoid Response and Safety in Anti-Neutrophil Cytoplasmic Antibody-Associated Vasculitis and Juvenile Dermatomyositis", Steroids, 140:159-166, (2018).
Conklin, LS et al., "039 Defining Serum CCL22 and Trefoil Factor 3 (TFF3) as Pharmacodynamic Biomarkers for Use in a Proof-of-Concept Clinical Trial of Vamorolone in Paediatric Ulcerative Colitis", Arch Dis Child, 104:e17, (2019).

(56) References Cited

OTHER PUBLICATIONS

Dang, U. et al., "Serum Biomarkers Associated with Baseline Clinical Severity in Young Steroid-Naive Duchenne Muscular Dystrophy Boys", Human Molecular Genetics, 29(15):2481-2495, (2020).
EMFLAZA™ (Product Label), Prescribing Information, 26 pages, (Revised: Feb. 2017).
EP Patent Application No. 09767367.7; File History Download, dated Apr. 13, 2012; 219 pages.
EP Patent Application No. 11191434.7; European Search Report, dated Mar. 27, 2012; 12 pages.
Guglieri, M. et al., "P.336Vision Dmd: A Phase IIb Randomized, Double-Blind, Parallel Group, Placebo- and Active-Controlled Study to Assess the Efficacy and Safety of Vamorolone in Boys with Duchenne Muscular Dystrophy", Neuromuscul. Dis., 29(1):S165, Abstract, (2019).
Guglieri, M. et al., "Vision DMD: A Drug Development Program for Vamorolone in Duchenne Muscular Dystrophy", Neuromuscul. Dis., 1(27):S17, (2017).
Guglieri, M. et al., "Vision DMD: Vamorolone (VBP15) Drug Development Program for Duchenne Muscular Dystrophy", European J. Paediatric Neur., 21(1):E238, Abstract, (2017).
Guglieri, M. et al., "Vamorolone Versus Placebo and Prednisone in Duchenne Muscular Dystrophy: Results from a 24-Week Double-Blind Randomized Trial", Neuromuscul. Dis., 31., (2021).
Guglieri, M., et al., "Vision DMD: Vamorolone Drug Development Program for Duchenne Muscular Dystrophy." Neuromuscul. Dis., 26:S156, Abstract, (2016).
Hathout, Y. et al., "Serum Pharmacodynamic Biomarkers for Chronic Corticosteroid Treatment of Children", Scientific Reports, 6:31727, 10 pages, (2016).
Hathout, Y. et al., "Biomarkers for Muscle Disease Gene Therapy", Muscle Gene Therapy, 239-252, (2019).
Hathout, Y. et al., "Disease-Specific and Glucocorticoid-Responsive Serum Biomarkers for Duchenne Muscular Dystrophy", Scientific Reports, 9:12167, 13 pages, (2019).
Hoffman, E. et al., "Clinical Trial Highlights: O. 3a 2.5-Years of Vamorolone Treatment in Duchenne Muscular Dystrophy: Results of an Open Label Long-Term Extension", Neuromuscul. Dis., 31:S48, (2021).
Hoffman, E. et al., "DMD-Treatment: EP. 147 2.5-Years of Vamorolone Treatment in Duchenne Muscular Dystrophy: Results of an Open Label Long-Term Extension", Neuromuscul. Dis., 31:S93-S94, (2021).
Hoffman, E. et al., "Phase 1 Trial of Vamorolone, a First-in-Class Steroid, Shows Improvements in Side Effects via Biomarkers Bridged to Clinical Outcomes", Steroids, 134:43-52 with supplemental materials, 18 pages, (2018).
Hoffman, E. et al., "Phase 1 Trial of Vamorolone, a First-in-Class Steroid, Shows Improvements in Side Effects via Biomarkers Bridged to Clinical Outcomes", Steroids, 134:43-52, (2018).
Hoffman, E. et al., "Vamorolone Trial in Duchenne Muscular Dystrophy Shows Dose-Related Improvement of Muscle Function", Neurology, 93(13):e1312-e1323, (2019).
Hoffman, E., "The Discovery of Dystrophin, The Protein Product of the Duchenne Muscular Dystrophy Gene", The FEBS Journal, 287(18):3879-3887, (2020).
Hoffman, E., "Causes of Clinical Variability in Duchenne and Becker Muscular Dystrophies and Implications for Exon Skipping Therapies", Acta Myologica, 39(4):179-186, (2020).
Hoffman, E., "Pharmacotherapy of Duchenne Muscular Dystrophy", Pediatric Pharmacotherapy, Handbook of Experimental Pharmacology, 25-37, (2019).
Hoffman, P. et al., CCDC Access Structure, Database Identifier SICZIQ, Deposition No. 1557034, retrieved from https://www.ccdc.cam.ac.uk/structures/Search?Ccdcid=1557034&DatabaseToSearch=Published on Mar. 14, 2022; 5 pages, (deposited on Jun. 19, 2017).
Judge, D. et al., "Pathophysiology and therapy of cardiac dysfunction in Duchenne muscular dystrophy", Am J Cardiovasc Drugs, 11(5):287-294, (2011).
Li, X. et al., "Exposure-Response Analysis of Vamorolone (VBP15) in Boys With Duchenne Muscular Dystrophy", J. Clin. Pharmacol., 60(10):1385-1396, (2020).
Mah, J. et al., "Efficacy and Safety of Vamorolone in Duchenne Muscular Dystrophy: A 30-Month Nonrandomized Controlled Open-Label Extension Trial", JAMA Network Open, 5(1):e2144178, 16 pages, (2022).
Mah, J. et al., "Vamorolone Versus Corticosteroid Real-World Experience: Comparisons of 2-Year Treatment Period with NorthStar UK Network and CINRG Duchenne Natural History Study", Neuromuscul. Dis., 31, (2021).
MX Patent Application No. 2010012976; Letter Reporting First Office Action, dated Apr. 3, 2013; 4 pages.
Nagaraju, K. et al., "DMD Clinical Therapies I: P. 114Vamorolone as a Replacement for Corticosteroids in Duchenne Muscular Dystrophy: Phase 2a Results in 48 DMD Boys", Neuromuscul. Dis., 28:S63-S64, (2018).
NZ Patent Application No. 589444; Examination Report, dated Dec. 20, 2011; 2 pages.
NZ Patent Application No. 589444; First Official Action, dated Apr. 19, 2011; 2 pages.
NZ Patent Application No. 589444; Response to Office Action, dated Nov. 30, 2011; 35 pages.
NZ Patent Application No. 589444; Second Official Action, dated Oct. 25, 2012; 2 pages.
NZ Patent Application No. 603107; Specification as filed, dated Oct. 18, 2012; 76 pages.
RAYOS (Product Label), Prescribing Information, 16 pages, (Revised: Jul. 2012).

NON-HORMONAL STEROID MODULATORS OF NF-KB FOR TREATMENT OF DISEASE

This application is a continuation of application Ser. No. 16/226,061, filed Dec. 19, 2018, now allowed, which is a continuation of application Ser. No. 15/483,863, filed Apr. 10, 2017, issued as U.S. Pat. No. 10,206,933 on Feb. 19, 2019, which is a divisional of application Ser. No. 15/229,947, filed Aug. 5, 2016, issued as U.S. Pat. No. 9,649,320 on May 16, 2017, which is a continuation of application Ser. No. 14/164,779, filed Jan. 27, 2014, issued as U.S. Pat. No. 9,434,758 on Sep. 6, 2016, which is a divisional of application Ser. No. 13/678,253, filed Nov. 15, 2012, issued as U.S. Pat. No. 8,673,887 on Mar. 18, 2014, which is a divisional of application Ser. No. 13/327,628, filed Dec. 15, 2011, issued as U.S. Pat. No. 8,334,279 on Dec. 18, 2012, which is a divisional of application Ser. No. 12/473,921, filed May 28, 2009, issued as U.S. Pat. No. 8,207,151 on Jun. 26, 2012, which claims the benefit of priority of U.S. Provisional Application No. 61/056,715, filed May 28, 2008, the disclosures of which are hereby incorporated by reference as if written herein in their entireties.

This invention was made with government support under grant Number HD053177 awarded by the National Institutes of Health and grant number W81XWH-05-1-0616 awarded by the U.S. Department of the Army. The government has certain rights in the invention.

Disclosed herein are new non-hormonal steroid compounds and compositions and their application as pharmaceuticals for the treatment of disease. Methods of modulation of NF-κB activity in a human or animal subject are also provided for the treatment of diseases mediated by NF-κB.

Muscular wasting diseases, such as muscular dystrophies, are a group of degenerative diseases that culminate in progressive skeletal muscle wasting leading to muscle weakness, a high incidence of bone fracture, wheelchair dependence, and in some cases death. Of the muscular dystrophies, Duchenne muscular dystrophy is the most severe and most widely recognized. Another muscular wasting disease which shows similar symptoms, although less severe than Duchenne muscular dystrophy, is Becker muscular dystrophy. Even though the defective dystrophin gene causing both Duchenne muscular dystrophy and Becker muscular dystrophy has been known for over 20 years, a cure is still lacking.

Several catabolic factors that act to destroy host tissues during the cachectic process have been identified. It appears that the oversecretion of inflammatory cytokines, specifically tumor necrosis factor-alpha (TNF-α), is one of the most likely causes of cachexia. Specifically, TNF-α can mimic most of the abnormalities that occur in cachexia such as weight loss, anorexia, increased thermogenesis, changes in lipid metabolism, insulin resistance, and muscle wasting.

Muscle atrophy can also be induced by the loss of innervation or damage to innervation of the muscle tissue. Diseases such as chronic neuropathy and motor neuron disease can cause damage to innervation. Physical injury to the nerve can also lead to damage to the innervation of the muscle tissue. Alternatively, muscle atrophy can be the result of environmental conditions such as during spaceflight or as a result of aging or extended bed rest. Under these environmental conditions, the muscles do not bear the usual weight load, resulting in muscle atrophy from disuse. Specifically, during muscle disuse, intracellular processes activated to induce proteolysis, mainly through the ATP dependent ubiquitin proteasome pathway, which regulates the NF-κB pathway.

NF-κB is known to mediate extracellular signals responsible for the induction of genes involved in pro-inflammatory responses. NF-κB is sequestered in the cytoplasm of most non-stimulated cells through a non-covalent interaction with one of several proteins known as inhibitors of kappa-beta (IκBs) (May & Ghosh, (1997) Semin. Cancer. Biol. 8, 63-73; May & Ghosh, (1998) Immunol. Today 19, 80-88; Ghosh et al., (1998) Annu. Rev. Immunol. 16, 225-260). Cellular stimuli associated with pro-inflammatory responses such as TNF-α activate kinases, which in turn activate NF-κB by phosphorylating IκBs. The kinases that phosphorylate IκBs are called IκB kinases (IKKs).

Phosphorylation targets IκBs for subsequent ubiquitination and degradation. This degradation of IκBs reveals the nuclear localization signal on NF-κB, allowing nuclear accumulation of activation, which leads to binding of DNA and control of specific gene expression. Phosphorylation of IκB is therefore an important step in the regulation of NF-κB downstream of many stimuli, although other mechanisms can lead to the activation of functional NF-κB.

The identification and characterization of kinases that phosphorylate IκBs has led to a better understanding of signaling pathways involving NF-κB activation. Several different subtypes of IKK have been identified thus far. IKKα was initially identified as an IκB kinase induced by TNF-α stimulation in HeLa cells (DiDonato et al., (1997) Nature 388, 548-554). Another IκB kinase homologous to IKKα was identified, termed IKKβ, and determined to be the major IκB kinase induced following TNFα stimulation (Takeda et al., (1999) Science 284, 313-316; U.S. Pat. No. 6,030,834, issued to Pots et al. (2000); U.S. Pat. No. 5,939,302, issued to Woronicz et al. (1999)). IKKα and IKKβ have an overall homology of 52% and a 65% homology in the kinase domain (Zandi et al., (1997) Cell 91, 243-252).

IκB protein kinases (IKKs) phosphorylate IκB s at specific serine residues. Specifically, they phosphorylate serines 32 and 36 of IκB (Traenckner et al., (1995) EMBO J. 14, 2876-2883; DiDonato et al., (1996) Mol. Cell. Biol. 16, 1295-1304). Phosphorylation of both sites is required to efficiently target IκBa for degradation. Furthermore, activation of IKKα and IKKβ is usually in response to NF-κB activating agents including phorbol 12-myristate 13-acetate (PMA), lipopolysaccharide (LPS), interleukin-1 (IL-1), TNF-α, reactive oxygen species, and DNA damaging agents. Mutant IKKα and IKKβ, which are catalytically inactive, can be used to block NF-κB stimulation. IκB kinases are therefore essential in the regulation of NF-κB activation processes downstream of inflammatory stimuli. In other pathways, IκB kinases may not be important.

IKKα and IKKβ have distinct structural motifs including an amino terminal serine-threonine kinase domain separated from a carboxyl proximal helix-loop-helix domain by a leucine zipper domain. These structural characteristics are unlike other kinases, and the non-catalytic domains are thought to be involved in protein-protein interactions. As such, proteins which bind to IKKs should be capable of regulating the activity of NF-κB and potentially regulating downstream events such as induction of NF-κB. For instance, NEMO (NF-κB Essential Modulator) is a protein which has been identified to bind to IKKs and facilitate kinase activity (Yamaoke et al., (1998) Cell 93, 1231-1240; Rothwarf et al., (1998) Nature 395, 287-300).

In vivo studies have shown that chronic NF-κB activation is associated with muscular wasting diseases such as Duchenne muscular dystrophy, and is further illustrated in US 2007/0225315 (Mar. 15, 2007). Specifically, muscle wasting was largely prevented in subjects that were heterozygous for the p65/RelA NF-κB subunit. An injection of an NF-κB activation inhibitor peptide was found to inhibit the dystrophic phenotype in affected mice subjects. Without being bound by a particular theory, it appears that chronic activation of NF-κB is required for the muscle wasting symptoms of Duchenne muscular dystrophy. As such, a drug-based therapy targeting NF-κB can be an effective strategy to treat Duchenne muscular dystrophy, as well as other forms of muscular wasting diseases.

In general, muscular wasting diseases may be treated in accordance with the present disclosure with a direct or indirect modulator of NF-κB. Indirect modulators of NF-κB include, for example, inhibitors of IκB kinases (IKKs) such as IKKα inhibitors and IKKβ inhibitors, and inhibitors functioning directly upstream from IKKs in the signaling pathway such as inhibitors of phosphoinositide dependent kinase (PDK) and inhibitors of Akt (also referred to as PKB).

As noted above, one suitable approach for modulating the NF-κB pathway is by binding to one of the IκB protein kinases (IKKs). By binding the IKKs, phosphorylation of IκB s is blocked and NF-κB cannot be activated. In one embodiment, direct inhibiting compounds of IKK catalytic activity can be administered for the purpose of blocking the NF-κB pathway and inhibiting a muscular wasting disease. Specifically, inhibitors of IKKα or their enantiomers, analogs, prodrugs, active metabolites, salts, and/or hydrates thereof can be administered to the subject for the purpose of inhibiting a muscular wasting disease.

Novel compounds and pharmaceutical compositions, certain of which have been found to modulate NF-κB have been discovered, together with methods of synthesizing and using the compounds including methods for the treatment of NF-κB-mediated diseases in a patient by administering the compounds.

In certain embodiments, disclosed herein are compounds having structural Formula I:

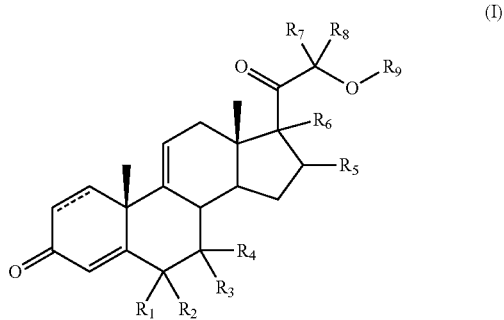

(I)

or a salt thereof, wherein:
said dashed line indicates an optional double bond;
$R_1$, $R_2$, $R_3$, and $R_4$ are each independently selected from the group consisting of hydrogen, unsubstituted lower alkyl, lower haloalkyl, and halogen;
$R_5$ is selected from the group consisting of hydrogen, lower alkyl, aryl, cycloalkyl, heterocycloalkyl, and heteroaryl, said lower alkyl, aryl, cycloalkyl, heterocycloalkyl, and heteroaryl being optionally substituted with one or more substituents selected from the group consisting of acyl, alkenyl, alkoxy, alkyl, alkynyl, amido, amino, aryl, aryloxy, cycloalkyl, haloalkoxy, haloalkyl, heteroalkyl, heteroaryl, hydroxy, perhaloalkoxy, and thiol;

$R_6$ is selected from the group consisting of hydrogen, hydroxyl, and lower alkyl, said lower alkyl being optionally substituted with one or more substituents selected from the group consisting of alkenyl, alkoxy, alkyl, alkynyl, aryl, aryloxy, haloalkoxy, haloalkyl, heteroalkyl, hydroxy, and thiol;
$R_7$ and $R_8$ are independently selected from the groups consisting of hydrogen, unsubstituted $C_{1-3}$ alkyl, or $R_7$ and $R_8$ can be taken together to form oxo or $C_{3-6}$ saturated cycloalkyl; and
$R_9$ is selected from the group consisting of hydrogen, acyl, and alkyl, said acyl and alkyl being optionally substituted with one or more substituents selected from the group consisting of acyl, alkenyl, alkoxy, alkyl, alkylamino, alkylthio, alkynyl, amido, amino, aryl, aryloxy, aroyl, carbamate, carboxyl, cyano, cycloalkyl, halogen, haloalkoxy, haloalkyl, heteroalkyl, heterocycloalkyl, heteroaryl, hydrazinyl, hydroxy, mercaptyl, nitro, oxo, perhaloalkoxy, sulfonate, alkylsulfonyl, N-sulfonamido, S-sulfonamido, and thiol.

In further embodiments, $R_7$ and $R_8$ are independently selected from the groups consisting of hydrogen, unsubstituted $C_2$-$C_3$ alkyl, or $R_7$ and $R_8$ can be taken together to form $C_3$-6 saturated cycloalkyl; $R_9$ is selected from the group consisting of hydrogen, acyl, and alkyl, said acyl and alkyl being optionally substituted with one or more substituents selected from the group consisting of acyl, alkenyl, alkoxy, alkyl, alkylamino, alkylthio, alkynyl, amino, aryl, aryloxy, aroyl, carbamate, cyano, cycloalkyl, halogen, haloalkoxy, haloalkyl, heteroalkyl, heterocycloalkyl, heteroaryl, hydrazinyl, hydroxy, mercaptyl, perhaloalkoxy, sulfonate, alkylsulfonyl, N-sulfonamido, S-sulfonamido, and thiol: if $R_1$ is hydrogen, methyl, —$CH_2F$, or fluoro, $R_2$, $R_3$, $R_4$, $R_5$, $R_7$, and $R_8$ are each hydrogen, and $R_6$ is hydroxyl, then $R_9$ is not hydrogen, formyl, unsubstituted $C_1$-$C_5$ alkylacyl, or benzoyl; if $R_1$ is hydrogen, methyl, —$CH_2F$, or fluoro, $R_2$, $R_3$, $R_4$, $R_7$, and $R_8$ are each hydrogen, $R_5$ is methyl, and $R_6$ is hydroxyl, then $R_9$ is not hydrogen, formyl, unsubstituted $C_1$-$C_5$ alkylacyl, trifluoroacetyl, —C(O)-adamantyl, or benzoyl; if $R_1$ is hydrogen, methyl, fluoro, or chloro, $R_2$, $R_3$, $R_4$, $R_6$, $R_7$, and $R_8$ are each hydrogen, and $R_5$ is methyl, then $R_9$ is not hydrogen, unsubstituted $C_1$-$C_5$ alkylacyl, or benzoyl; if said dashed line indicates a double bond, $R_1$, $R_2$, $R_3$, $R_4$, $R_7$, and $R_8$ are each hydrogen, and $R_5$ and $R_6$ are each methyl, then $R_9$ is not hydrogen, acetyl, or benzoyl; if said dashed line indicates a double bond, $R_1$, $R_2$, $R_3$, $R_4$, $R_5$, $R_7$, and $R_8$ are each hydrogen, and $R_6$ is ethyl, then $R_9$ is not acetyl; if said dashed line does not indicate a double bond, $R_1$ is hydrogen or fluoro, and $R_2$, $R_3$, $R_4$, $R_5$, $R_6$, $R_7$, and $R_8$ are each hydrogen, then $R_9$ is not hydrogen or acetyl; if $R_1$, $R_2$, $R_4$, $R_5$, $R_7$, and $R_8$ are each hydrogen, $R_3$ is methyl, and $R_6$ is hydroxyl, then $R_9$ is not hydrogen, formyl, unsubstituted $C_1$-$C_5$ alkylacyl, or benzoyl; and if $R_1$ and $R_2$ are each fluoro, $R_3$, $R_4$, $R_7$, and $R_8$ are each hydrogen, $R_5$ is methyl, and $R_6$ is hydroxyl, then $R_9$ is not acetyl.

In further embodiments, $R_5$ is selected from the group consisting of $C_2$-$C_8$ alkyl, aryl, cycloalkyl, heterocycloalkyl, and heteroaryl, said $C_2$-$C_8$ alkyl, aryl, cycloalkyl, heterocycloalkyl, and heteroaryl being optionally substituted with one or more substituents selected from the group consisting of acyl, alkenyl, alkoxy, alkyl, alkynyl, amido, amino, aryl, aryloxy, cycloalkyl, haloalkoxy, haloalkyl, heteroalkyl, heteroaryl, hydroxy, perhaloalkoxy, and thiol.

In further embodiments, $R_1$ and $R_3$ are each hydrogen; $R_2$ and $R_4$ are each independently selected from the group consisting of hydrogen, methyl, and fluorine; $R_5$ is selected from the group consisting of hydrogen, unsubstituted lower alkyl, and phenyl; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino, hydroxyl, and carboxyl.

In further embodiments, $R_2$ and $R_4$ are each hydrogen; $R_5$ is selected from the group consisting of hydrogen, unsubstituted lower alkyl, and phenyl; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino, hydroxyl, and carboxyl.

In further embodiments, $R_5$ is selected from the group consisting of hydrogen, methyl, and ethyl; $R_6$ is selected from the group consisting of hydrogen, hydroxyl, and methyl; and $R_9$ is selected from the group consisting of hydrogen, acetyl, and —C(O)CH$_2$CH$_2$CO$_2$H.

In further embodiments, $R_5$ is selected from the group consisting of unsubstituted C$_2$-C$_6$ alkyl and phenyl; $R_6$ is selected from the group consisting of hydrogen, hydroxyl, and methyl; and $R_9$ is selected from the group consisting of hydrogen, acetyl, and —C(O)CH$_2$CH$_2$CO$_2$H.

In further embodiments, $R_5$ is ethyl.

In further embodiments, said dashed line indicates an optional double bond; $R_1$, $R_2$, $R_3$, and $R_4$ are each independently selected from the group consisting of hydrogen, unsubstituted lower alkyl, lower haloalkyl, and halogen; $R_5$ is selected from the group consisting of hydrogen, lower alkyl, aryl, cycloalkyl, heterocycloalkyl, and heteroaryl, said lower alkyl, aryl, cycloalkyl, heterocycloalkyl, and heteroaryl being optionally substituted with one or more substituents selected from the group consisting of acyl, alkenyl, alkoxy, alkyl, alkynyl, amido, amino, aryl, aryloxy, cycloalkyl, haloalkoxy, haloalkyl, heteroalkyl, heteroaryl, hydroxy, perhaloalkoxy, and thiol; $R_6$ is selected from the group consisting of hydrogen, hydroxyl, and lower alkyl, said lower alkyl being optionally substituted with one or more substituents selected from the group consisting of alkenyl, alkoxy, alkyl, alkynyl, aryl, aryloxy, haloalkoxy, haloalkyl, heteroalkyl, hydroxy, and thiol; $R_7$ and $R_8$ are independently selected from the groups consisting of hydrogen, unsubstituted C$_{1-3}$ alkyl, or $R_7$ and $R_8$ can be taken together to form oxo or C$_{3-6}$ saturated cycloalkyl; and $R_9$ is selected from the group consisting of hydrogen, acyl, and alkyl, said acyl and alkyl being optionally substituted with one or more substituents selected from the group consisting of acyl, alkenyl, alkoxy, alkyl, alkylamino, alkylthio, alkynyl, amido, amino, aryl, aryloxy, aroyl, carbamate, carboxyl, cyano, cycloalkyl, halogen, haloalkoxy, haloalkyl, heteroalkyl, heterocycloalkyl, heteroaryl, hydrazinyl, hydroxy, mercaptyl, nitro, oxo, perhaloalkoxy, alkylsulfonyl, N-sulfonamido, S-sulfonamido, and thiol; if $R_1$, $R_2$, $R_3$, $R_4$, $R_7$, and $R_8$ are each hydrogen, $R_5$ is methyl, and $R_6$ is hydroxyl, then $R_9$ is not —C(O)CH$_2$CH$_2$CO$_2$H; if said dashed line does not indicate a double bond, $R_1$, $R_2$, $R_3$, $R_4$, $R_5$, $R_7$, and $R_8$ are each hydrogen, and $R_6$ is hydroxyl, then $R_9$ is not —C(O)CH$_2$CH$_2$CO$_2$H; if said dashed line indicates a double bond, $R_1$ is methyl, $R_2$, $R_3$, $R_4$, $R_5$, $R_7$, and $R_8$ are each hydrogen, and $R_6$ is hydroxyl, then $R_9$ is not —C(O)CH$_2$CH$_2$CO$_2$H; if $R_1$, $R_2$, $R_3$, $R_4$, $R_5$, $R_7$, and $R_8$ are each hydrogen and $R_6$ is hydroxyl, then $R_9$ is not hydrogen or acetyl; if said dashed line does not indicate a double bond, $R_1$ is fluorine, $R_2$, $R_3$, $R_4$, $R_7$, and $R_8$ are each hydrogen, $R_5$ is methyl, and $R_6$ is hydroxyl, then $R_9$ is not hydrogen or acetyl; and if said dashed line does not indicate a double bond, $R_1$ is methyl, $R_2$, $R_3$, $R_4$, $R_5$, $R_7$, and $R_8$ are each hydrogen, and $R_6$ is hydroxyl, then $R_9$ is not acetyl.

In further embodiments, $R_7$ and $R_8$ are independently selected from the groups consisting of hydrogen, unsubstituted C$_2$-C$_3$ alkyl, or $R_7$ and $R_8$ can be taken together to form C$_3$-6 saturated cycloalkyl; $R_9$ is selected from the group consisting of hydrogen, acyl, and alkyl, said acyl and alkyl being optionally substituted with one or more substituents selected from the group consisting of acyl, alkenyl, alkoxy, alkyl, alkylamino, alkylthio, alkynyl, amino, aryl, aryloxy, aroyl, carbamate, cyano, cycloalkyl, halogen, haloalkoxy, haloalkyl, heteroalkyl, heterocycloalkyl, heteroaryl, hydrazinyl, hydroxy, mercaptyl, perhaloalkoxy, alkylsulfonyl, N-sulfonamido, S-sulfonamido, and thiol; if $R_1$ is hydrogen, methyl, —CH$_2$F, or fluoro, $R_2$, $R_3$, $R_4$, $R_5$, $R_7$, and $R_8$ are each hydrogen, and $R_6$ is hydroxyl, then $R_9$ is not hydrogen, formyl, unsubstituted C$_1$-C$_5$ alkylacyl, or benzoyl; if $R_1$ is hydrogen, methyl, —CH$_2$F, or fluoro, $R_2$, $R_3$, $R_4$, $R_7$, and $R_8$ are each hydrogen, $R_5$ is methyl, and $R_6$ is hydroxyl, then $R_9$ is not hydrogen, formyl, unsubstituted C$_1$-C$_5$ alkylacyl, trifluoroacetyl, —C(O)-adamantyl, or benzoyl; if $R_1$ is hydrogen, methyl, fluoro, or chloro, $R_2$, $R_3$, $R_4$, $R_6$, $R_7$, and $R_8$ are each hydrogen, and $R_5$ is methyl, then $R_9$ is not hydrogen, unsubstituted C$_1$-C$_5$ alkylacyl, or benzoyl; if said dashed line indicates a double bond, $R_1$, $R_2$, $R_3$, $R_4$, $R_7$, and $R_8$ are each hydrogen, and $R_5$ and $R_6$ are each methyl, then $R_9$ is not hydrogen, acetyl, or benzoyl; if said dashed line indicates a double bond, $R_1$, $R_2$, $R_3$, $R_4$, $R_5$, $R_7$, and $R_8$ are each hydrogen, and $R_6$ is ethyl, then $R_9$ is not acetyl; if said dashed line does not indicate a double bond, $R_1$ is hydrogen or fluoro, and $R_2$, $R_3$, $R_4$, $R_5$, $R_6$, $R_7$, and $R_8$ are each hydrogen, then $R_9$ is not hydrogen or acetyl; if $R_1$, $R_2$, $R_4$, $R_5$, $R_7$, and $R_8$ are each hydrogen, $R_3$ is methyl, and $R_6$ is hydroxyl, then $R_9$ is not hydrogen, formyl, unsubstituted C$_1$-C$_5$ alkylacyl, or benzoyl; and if $R_1$ and $R_2$ are each fluoro, $R_3$, $R_4$, $R_7$, and $R_8$ are each hydrogen, $R_5$ is methyl, and $R_6$ is hydroxyl, then $R_9$ is not acetyl.

In further embodiments, $R_5$ is selected from the group consisting of C$_2$-C$_8$ alkyl, aryl, cycloalkyl, heterocycloalkyl, and heteroaryl, said C$_2$-C$_8$ alkyl, aryl, cycloalkyl, heterocycloalkyl, and heteroaryl being optionally substituted with one or more substituents selected from the group consisting of acyl, alkenyl, alkoxy, alkyl, alkynyl, amido, amino, aryl, aryloxy, cycloalkyl, haloalkoxy, haloalkyl, heteroalkyl, heteroaryl, hydroxy, perhaloalkoxy, and thiol.

In further embodiments, $R_1$ and $R_3$ are each hydrogen; $R_2$ and $R_4$ are each independently selected from the group consisting of hydrogen, methyl, and fluorine; $R_5$ is selected from the group consisting of hydrogen, unsubstituted lower alkyl, and phenyl; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino, hydroxyl, and carboxyl.

In further embodiments, $R_2$ and $R_4$ are each hydrogen; $R_5$ is selected from the group consisting of hydrogen, unsubstituted lower alkyl, and phenyl; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino, hydroxyl, and carboxyl.

In further embodiments, $R_5$ is selected from the group consisting of hydrogen, methyl, and ethyl; $R_6$ is selected from the group consisting of hydrogen, hydroxyl, and methyl; and $R_9$ is selected from the group consisting of hydrogen, acetyl, and —C(O)CH$_2$CH$_2$CO$_2$H.

In further embodiments, $R_5$ is selected from the group consisting of unsubstituted C$_2$-C$_6$ alkyl and phenyl; $R_6$ is selected from the group consisting of hydrogen, hydroxyl, and methyl; and $R_9$ is selected from the group consisting of hydrogen, acetyl, and —C(O)CH$_2$CH$_2$CO$_2$H.

In further embodiments, $R_5$ is ethyl.

In further embodiments, said dashed line indicates an optional double bond; $R_1$, $R_2$, $R_3$, and $R_4$ are each independently selected from the group consisting of hydrogen, unsubstituted lower alkyl, lower haloalkyl, and halogen; $R_5$ is selected from the group consisting of hydrogen, lower alkyl, aryl, cycloalkyl, heterocycloalkyl, and heteroaryl, said lower alkyl, aryl, cycloalkyl, heterocycloalkyl, and heteroaryl being optionally substituted with one or more substituents selected from the group consisting of acyl, alkenyl, alkoxy, alkyl, alkynyl, amido, amino, aryl, aryloxy, cycloalkyl, haloalkoxy, haloalkyl, heteroalkyl, heteroaryl, hydroxy, perhaloalkoxy, and thiol; $R_6$ is selected from the group consisting of hydrogen, hydroxyl, and lower alkyl, said lower alkyl being optionally substituted with one or more substituents selected from the group consisting of alkenyl, alkoxy, alkyl, alkynyl, aryl, aryloxy, haloalkoxy, haloalkyl, heteroalkyl, hydroxy, and thiol; $R_7$ and $R_8$ are independently selected from the groups consisting of hydrogen, unsubstituted $C_2$-$C_3$ alkyl, or $R_7$ and $R_8$ can be taken together to form $C_{3-6}$ saturated cycloalkyl; $R_9$ is selected from the group consisting of hydrogen, acyl, and alkyl, said acyl and alkyl being optionally substituted with one or more substituents selected from the group consisting of acyl, alkenyl, alkoxy, alkyl, alkylamino, alkylthio, alkynyl, amino, aryl, aryloxy, aroyl, carbamate, cyano, cycloalkyl, halogen, haloalkoxy, haloalkyl, heteroalkyl, heterocycloalkyl, heteroaryl, hydrazinyl, hydroxy, mercaptyl, perhaloalkoxy, sulfonate, alkylsulfonyl, N-sulfonamido, S-sulfonamido, and thiol; if $R_1$ is hydrogen, methyl, —CH$_2$F, or fluoro, $R_2$, $R_3$, $R_4$, $R_5$, $R_7$, and $R_8$ are each hydrogen, and $R_6$ is hydroxyl, then $R_9$ is not hydrogen, formyl, unsubstituted $C_1$-$C_5$ alkylacyl, or benzoyl; if $R_1$ is hydrogen, methyl, —CH$_2$F, or fluoro, $R_2$, $R_3$, $R_4$, $R_7$, and $R_8$ are each hydrogen, $R_5$ is methyl, and $R_6$ is hydroxyl, then $R_9$ is not hydrogen, formyl, unsubstituted $C_1$-$C_5$ alkylacyl, trifluoroacetyl, —C(O)-adamantyl, or benzoyl; if $R_1$ is hydrogen, methyl, fluoro, or chloro, $R_2$, $R_3$, $R_4$, $R_6$, $R_7$, and $R_8$ are each hydrogen, and $R_5$ is methyl, then $R_9$ is not hydrogen, unsubstituted $C_1$-$C_5$ alkylacyl, or benzoyl; if said dashed line indicates a double bond, $R_1$, $R_2$, $R_3$, $R_4$, $R_7$, and $R_8$ are each hydrogen, and $R_5$ and $R_6$ are each methyl, then $R_9$ is not hydrogen, acetyl, or benzoyl; if said dashed line indicates a double bond, $R_1$, $R_2$, $R_3$, $R_4$, $R_5$, $R_7$, and $R_8$ are each hydrogen, and $R_6$ is ethyl, then $R_9$ is not acetyl; if said dashed line does not indicate a double bond, $R_1$ is hydrogen or fluoro, and $R_2$, $R_3$, $R_4$, $R_5$, $R_6$, $R_7$, and $R_8$ are each hydrogen, then $R_9$ is not hydrogen or acetyl; if $R_1$, $R_2$, $R_4$, $R_5$, $R_7$, and $R_8$ are each hydrogen, $R_3$ is methyl, and $R_6$ is hydroxyl, then $R_9$ is not hydrogen, formyl, unsubstituted $C_1$-$C_5$ alkylacyl, or benzoyl; and if $R_1$ and $R_2$ are each fluoro, $R_3$, $R_4$, $R_7$, and $R_8$ are each hydrogen, $R_5$ is methyl, and $R_6$ is hydroxyl, then $R_9$ is not acetyl.

In further embodiments, $R_1$ and $R_3$ are each hydrogen; $R_2$ and $R_4$ are each independently selected from the group consisting of hydrogen, methyl, and fluorine; $R_5$ is selected from the group consisting of hydrogen, unsubstituted lower alkyl, and phenyl; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino and hydroxyl.

In further embodiments, $R_2$ and $R_4$ are each hydrogen; $R_5$ is selected from the group consisting of hydrogen, unsubstituted lower alkyl, and phenyl; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino and hydroxyl.

In further embodiments, $R_5$ is selected from the group consisting of hydrogen, methyl, and ethyl; $R_6$ is selected from the group consisting of hydrogen, hydroxyl, and methyl; and $R_9$ is selected from the group consisting of hydrogen and acetyl.

In further embodiments, said dashed line indicates an optional double bond; $R_1$, $R_2$, $R_3$, and $R_4$ are each independently selected from the group consisting of hydrogen, unsubstituted lower alkyl, lower haloalkyl, and halogen; $R_5$ is selected from the group consisting of $C_2$-$C_8$ alkyl, aryl, cycloalkyl, heterocycloalkyl, and heteroaryl, said $C_2$-$C_8$ alkyl, aryl, cycloalkyl, heterocycloalkyl, and heteroaryl being optionally substituted with one or more substituents selected from the group consisting of acyl, alkenyl, alkoxy, alkyl, alkynyl, amido, amino, aryl, aryloxy, cycloalkyl, haloalkoxy, haloalkyl, heteroalkyl, heteroaryl, hydroxy, perhaloalkoxy, and thiol; $R_6$ is selected from the group consisting of hydrogen, hydroxyl, and lower alkyl, said lower alkyl being optionally substituted with one or more substituents selected from the group consisting of alkenyl, alkoxy, alkyl, alkynyl, aryl, aryloxy, haloalkoxy, haloalkyl, heteroalkyl, hydroxy, and thiol; $R_7$ and $R_8$ are independently selected from the groups consisting of hydrogen, unsubstituted $C_{1-3}$ alkyl, or $R_7$ and $R_8$ can be taken together to form oxo or $C_{3-6}$ saturated cycloalkyl; and $R_9$ is selected from the group consisting of hydrogen, acyl, and alkyl, said acyl and alkyl being optionally substituted with one or more substituents selected from the group consisting of acyl, alkenyl, alkoxy, alkyl, alkylamino, alkylthio, alkynyl, amido, amino, aryl, aryloxy, aroyl, carbamate, carboxyl, cyano, cycloalkyl, halogen, haloalkoxy, haloalkyl, heteroalkyl, heterocycloalkyl, heteroaryl, hydrazinyl, hydroxy, mercaptyl, nitro, oxo, perhaloalkoxy, sulfonate, alkylsulfonyl, N-sulfonamido, S-sulfonamido, and thiol.

In further embodiments, $R_1$ and $R_3$ are each hydrogen; $R_2$ and $R_4$ are each independently selected from the group consisting of hydrogen, methyl, and fluorine; $R_5$ is selected from the group consisting of unsubstituted $C_2$-$C_6$ alkyl and phenyl; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino, hydroxyl, and carboxyl.

In further embodiments, $R_2$ and $R_4$ are each hydrogen; $R_6$ is selected from the group consisting of hydrogen, hydroxyl, and methyl; $R_7$ and $R_8$ are each hydrogen; and $R_9$ is selected from the group consisting of hydrogen, acyl, and alkyl, said acyl and alkyl being optionally substituted with amino, hydroxyl, and carboxyl.

In further embodiments, $R_6$ is selected from the group consisting of hydrogen, hydroxyl, and methyl; and $R_9$ is selected from the group consisting of hydrogen, acetyl, and —C(O)CH$_2$CH$_2$CO$_2$H.

In further embodiments, $R_5$ is ethyl.

Certain compounds disclosed herein may possess useful NF-κB modulating activity, and may be used in the treatment or prophylaxis of a disease or condition in which NF-κB plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating NF-κB. Other embodiments provide methods for treating a NF-κB-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the modulation of NF-κB.

In certain embodiments, said NF-κB-mediated disease is selected from the group consisting of muscular dystrophy, arthritis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, muscle wasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, and hearing loss.

In further embodiments, said disease is said NF-κB-mediated disease is asthma or chronic obstructive pulmonary disease.

In further embodiments, said NF-κB-mediated is Sjogren's syndrome.

In further embodiments, said NF-κB-mediated is arthritis.

In further embodiments, said NF-κB-mediated is muscular wasting.

In further embodiments, said muscular wasting disease is muscular dystrophy.

In further embodiments, said muscular dystrophy is selected from the group consisting of Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In further embodiments, said muscular dystrophy is Duchenne muscular dystrophy.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term arlyoxy as used herein, alone or in combination, refers to an aryl group attached to the parent molecular moiety through an oxy.

The terms "benzo" and "benz," as used herein, alone or in combination, refer to the divalent group C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 3 to 7 carbon atoms. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzindolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "NF-κB-mediated disease," refers to a disease in which NF-κB plays an active role in the disease pathology. NF-κB-mediated diseases include diseases in which multiple biological pathways and/or processes in addition to NF-κB-mediated processes contribute to the disease pathology. A NF-κB-mediated disease may be completely or partially mediated by modulating the activity or amount of NF-κB. In particular, a NF-κB-mediated disease is one in which modulation of NF-κB results in some effect on the underlying disease e.g., administration of a NF-κB modulator results in some improvement in at least some of the patients being treated. The term "NF-κB-mediated disease" also refers to the following diseases, even though the compounds disclosed herein exert their effects through biological pathways and/or processes other than NF-κB: muscular dystrophy, arthritis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, muscle wasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, and hearing loss.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"NF-κB modulator is used herein to refer to a compound that exhibits an $EC_{50}$ with respect to NF-κB activity of no more than about 100 μM and more typically not more than about 50 μM, as measured in the NF-κB inhibitor assays described generally hereinbelow. "$EC_{50}$" is that concentration of modulator which either activates or reduces the activity or increases or decreases the amount of an enzyme (e.g., (NF-κB)) to half-maximal level. Certain compounds disclosed herein have been discovered to exhibit modulatory activity against NF-κB. In certain embodiments, compounds will exhibit an $EC_{50}$ with respect to NF-κB of no more than about 10 μM; in further embodiments, compounds will exhibit an $EC_{50}$ with respect to NF-κB of no more than about 5 μM; in yet further embodiments, compounds will exhibit an $EC_{50}$ with respect to NF-κB of not more than about 1 μM; in yet further embodiments, compounds will exhibit an $EC_{50}$ with respect to NF-κB of not more than about 200 nM, as measured in the NF-κB assay described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The terms "therapeutically acceptable salt," or "salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, paratoluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

In certain embodiments, the salts may include hydrochloride, hydrobromide, sulfonate, citrate, tartrate, phosphonate, lactate, pyruvate, acetate, succinate, oxalate, fumarate, malate, oxaloacetate, methanesulfonate, ethanesulfonate, p-toluenesulfonate, benzenesulfonate and isethionate salts of compounds disclosed herein. A salt of a compound can be made by reacting the appropriate compound in the form of the free base with the appropriate acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes.

Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For oral or parenteral use, the compounds may be formulated as nanoparticle preparations. Such nanoparticle preparations can include, for example, nanoshere encapsulations of active compounds, inactive nanoparticles to which active compounds can be tethered, or nanoscale powders of active compounds. Nanoparticle preparations can be used to increase the bioavailability of the active compounds, control the rate of release of the active compounds, or deliver active compounds to a particular location in the body. See A. Dove, "An Easy Pill to Swallow", *Drug Discovery & Development Magazine:* 11(11), November, 2008, pp. 22-24.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating NF-κB-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of NF-κB-mediated disorders.

Specific diseases to be treated by the compounds, compositions, and methods disclosed herein include ageing, headache, pain, complex regional pain syndrome, cardiac hypertrophy, muscular dystrophy, muscle wasting, catabolic disorders, type 1 diabetes, type 2 diabetes, obesity, fetal growth retardation, hypercholesterolemia, atherosclerosis, heart disease, chronic heart failure, ischemia/reperfusion, stroke, cerebral aneurysm, angina pectoris, pulmonary disease, cystic fibrosis, acid-induced lung injury, pulmonary hypertension, chronic obstructive pulmonary disease, hyaline membrane disease, kidney disease, glomerular disease, alcoholic liver disease, leptospiriosis renal disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, arthritis, crohn's disease, colitis, ocular allergy, glaucoma, appendicitis, paget's disease, pancreatitis, periodonitis, endometriosis, inflammatory bowel disease, inflammatory lung disease, sepsis, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, traumatic brain injury, spinal cord injury, parkinson's disease, multiple sclerosis, rheumatic disease, alzheimer's disease, amyotropic lateral sclerosis, huntington's disease, retinal disease, cataracts, hearing loss, and cancer.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein in their entireties. Where any inconsistencies arise, material literally disclosed herein controls.

General Synthetic Methods for Preparing Compounds

The following schemes can be used to practice the present invention.

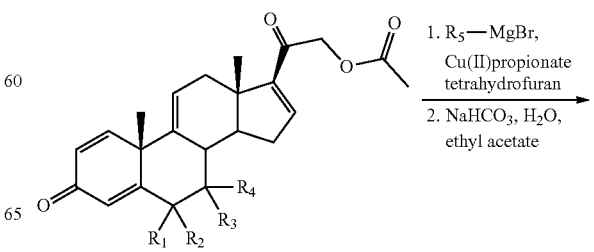

Scheme I

-continued
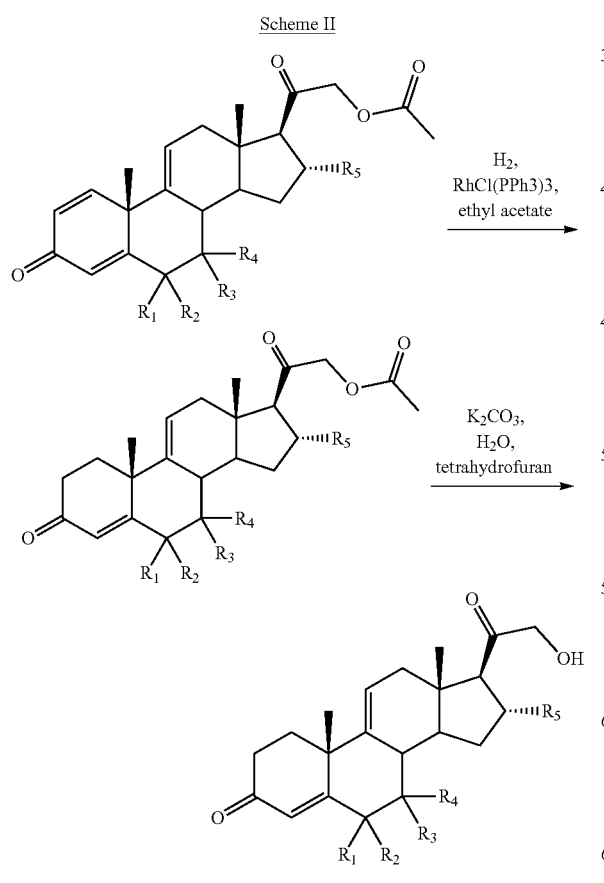
Examples 6-7, 23, and 28 can be synthesized according to scheme I.
Scheme II
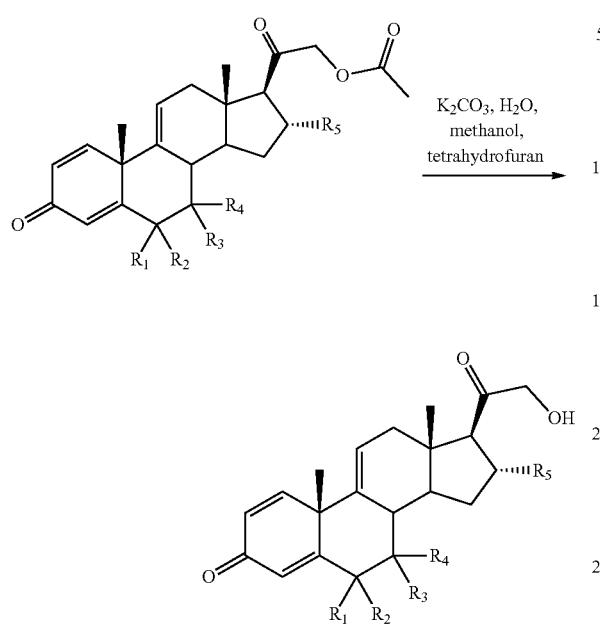
Examples 8 and 24-25 can be synthesized according to scheme II.
Scheme III
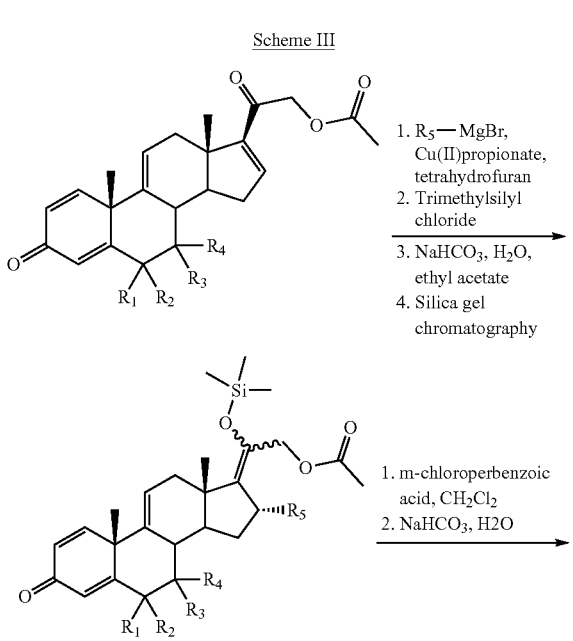
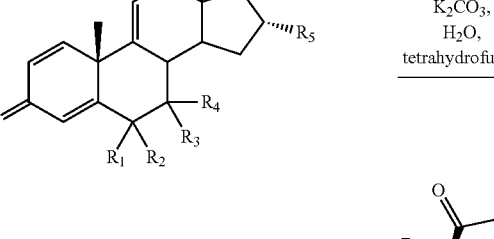
Examples 15, 22, and 27 can be synthesized according to scheme III.
Scheme IV

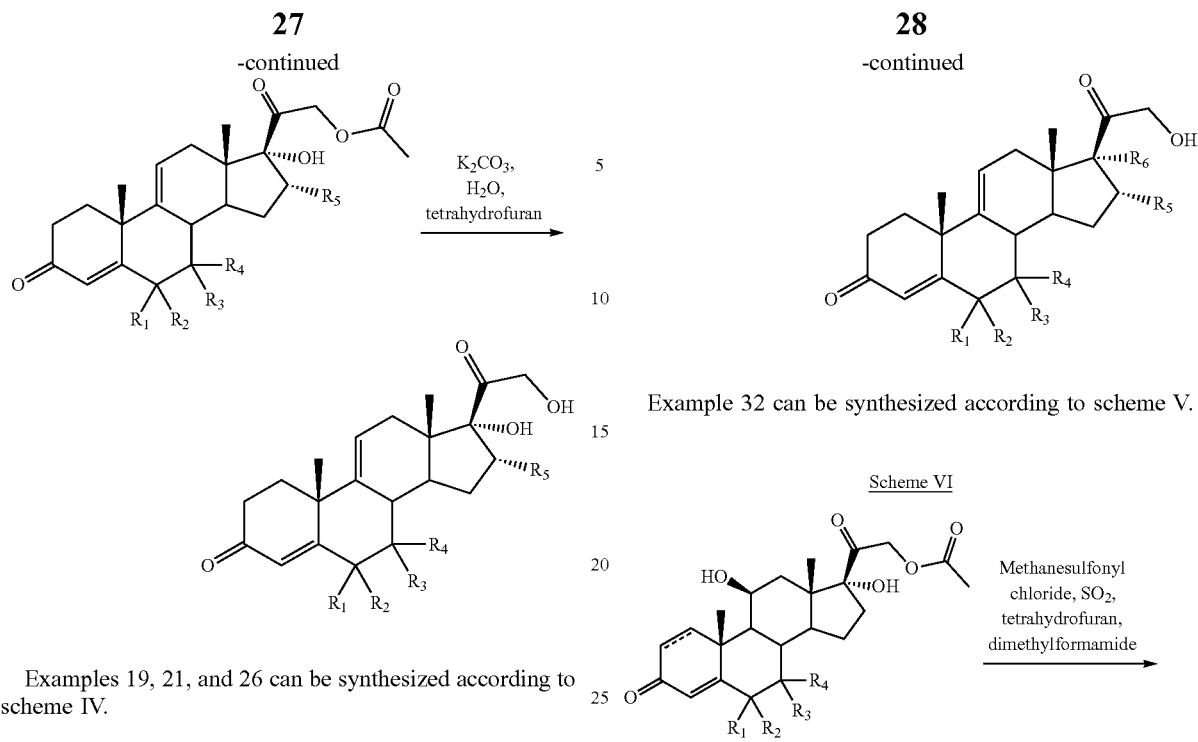
Examples 19, 21, and 26 can be synthesized according to scheme IV.
Example 32 can be synthesized according to scheme V.
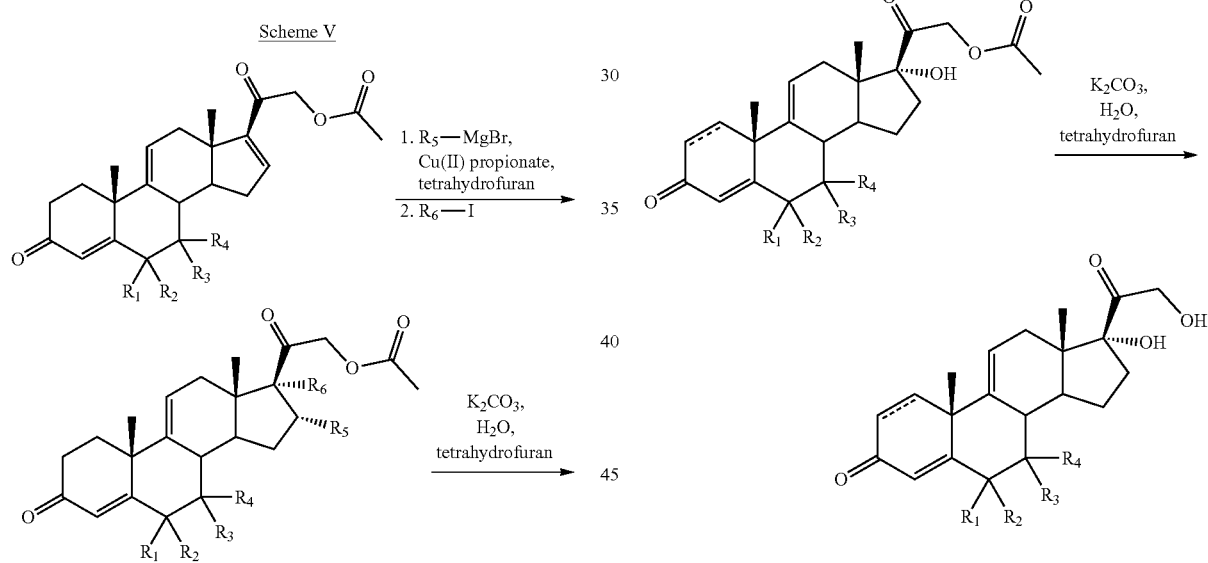
Examples 1-3 can be synthesized according to scheme VI.
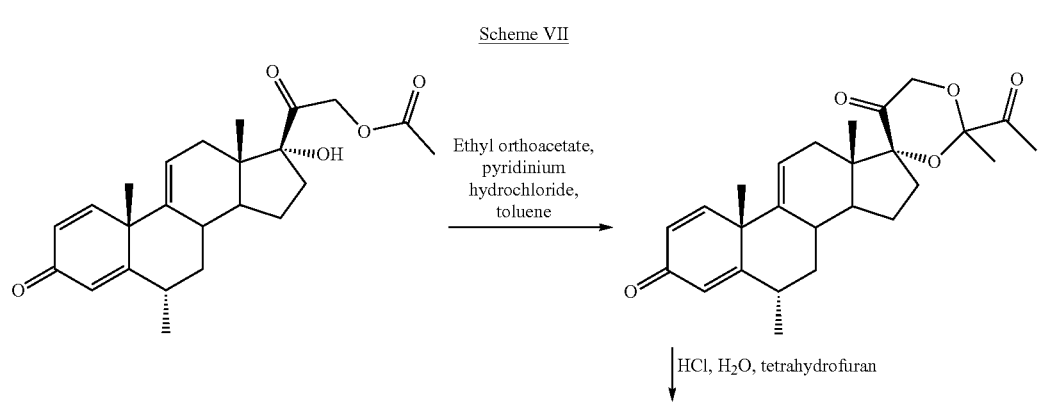

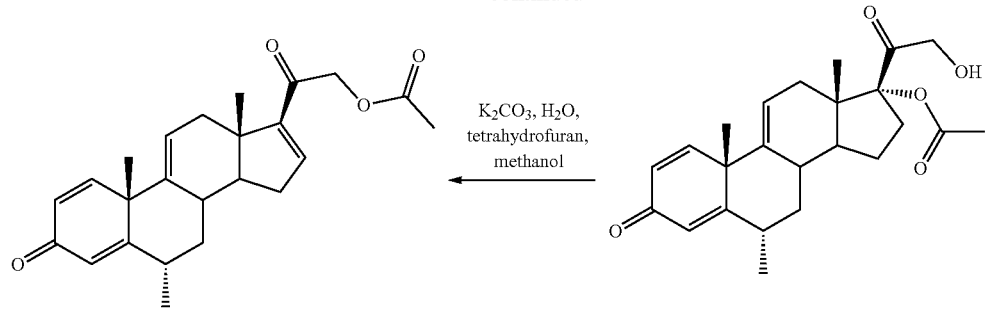

Preparation 1 can be synthesized according to scheme VII.

Preparation 1

2-oxo-2-((6S,10R,13S)-6,10,13-trimethyl-3-oxo-6,7,8,10,12,13,14,15-octahydro-3H-cyclopenta[a]phenanthren-17-yl)ethyl acetate

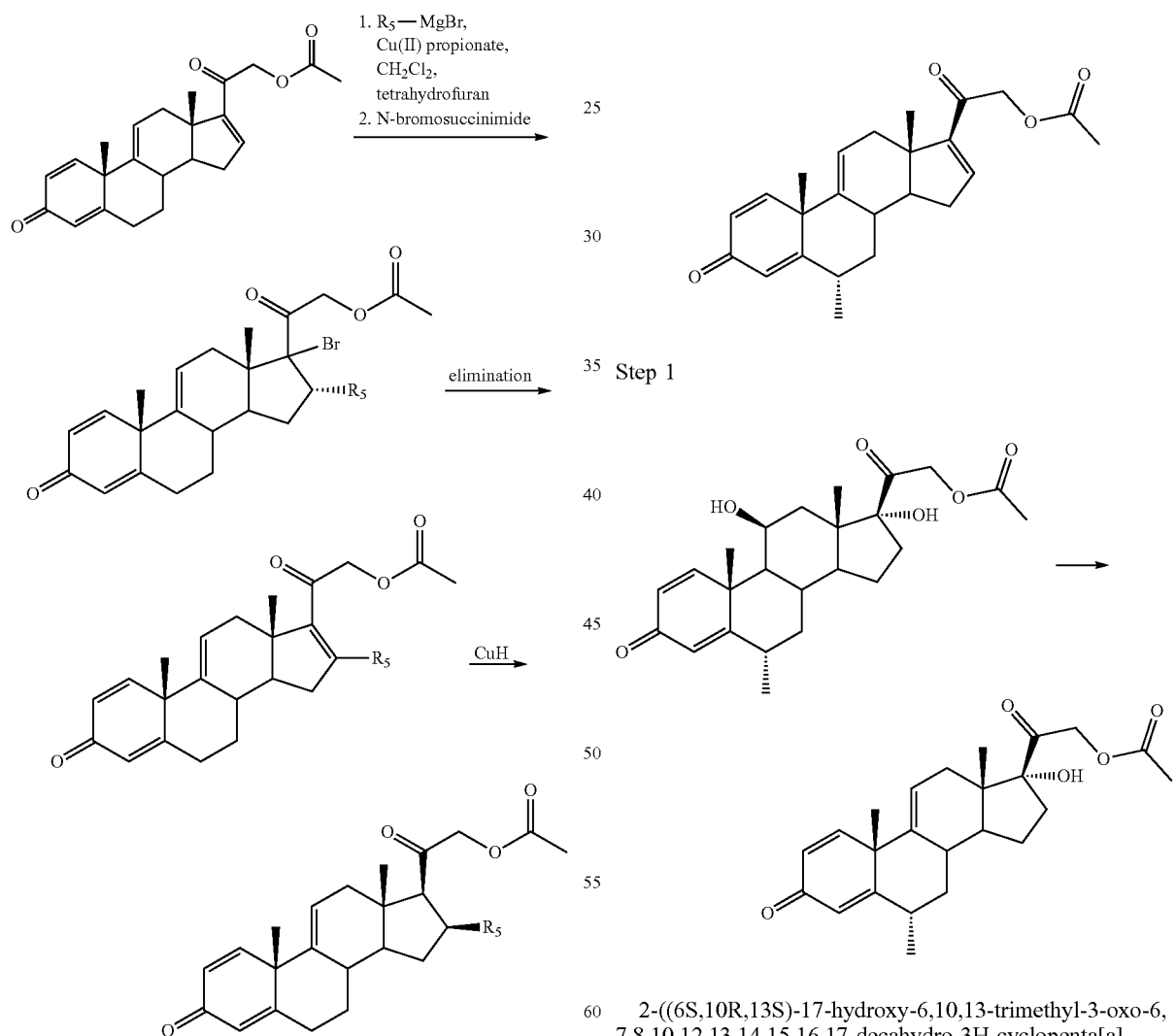

Step 1

2-((6S,10R,13S)-17-hydroxy-6,10,13-trimethyl-3-oxo-6,7,8,10,12,13,14,15,16,17-decahydro-3H-cyclopenta[a]phenanthren-17-yl)-2-oxoethyl acetate: (see Tetrahedron Letters, 2001, 42 (14): 2639-2642). Alternatively, methyl prednisolone 21-acetate is dissolved in a mixture of dimethylformamide and tetrahydrofuran and cooled in an ice bath. $SO_2$ is bubbled into methanesulfonyl chloride and the mixture is added dropwise to the solution containing the Example 16 can be synthesized according to scheme VIII.

The invention is further illustrated by the following examples. All IUPAC names were generated using CambridgeSoft's ChemDraw 10.0.

solution of methyl prednisolone 21-acetate. The title product can then be isolated by standard aqueous workup.

Step 2

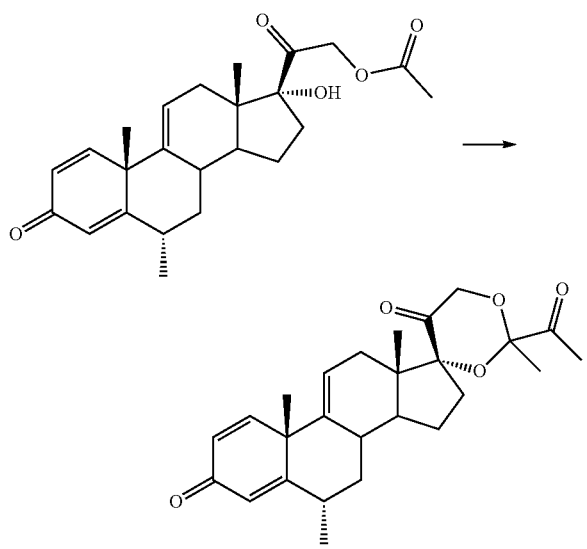

(2'R,4'R,6S,10R,13S)-2'-acetyl-2',6,10,13-tetramethyl-7,8,10,12,13,14,15,16-octahydrospiro[cyclopenta[a]phenanthrene-17,4'-[1,3]dioxane]-3,5'(6H)-dione: 2-((6S,10R,13S)-17-hydroxy-6,10,13-trimethyl-3-oxo-6,7,8,10,12,13,14,15,16,17-decahydro-3H-cyclopenta[a]phenanthren-17-yl)-2-oxoethyl acetate is dissolved in toluene and heated with 1.5 equivalents of ethyl orthoacetate and a trace of pyridinium hydrochloride. Ethanol is distilled off the reaction mixture to drive it to completion.

Step 3

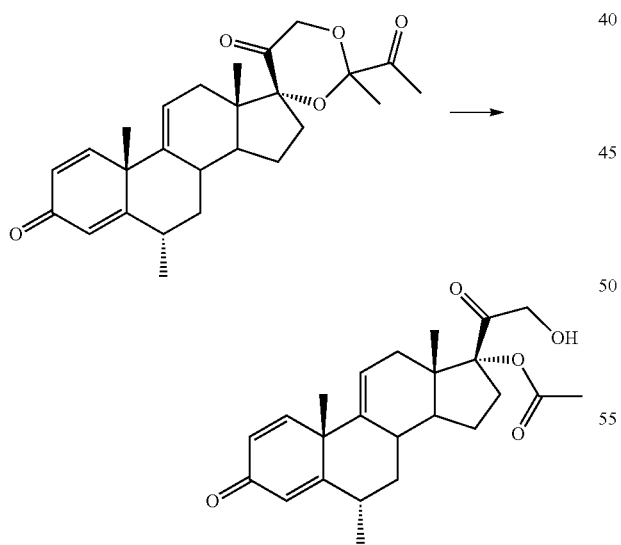

(6S,10R,13S)-17-(2-hydroxyacetyl)-6,10,13-trimethyl-3-oxo-6,7,8,10,12,13,14,15,16,17-decahydro-3H-cyclopenta[a]phenanthren-17-yl acetate: The reaction mixture from step 3 is concentrated, dissolved in tetrahydrofuran, and treated with dilute hydrochloric acid. Standard aqueous workup yields the title compound.

Step 4

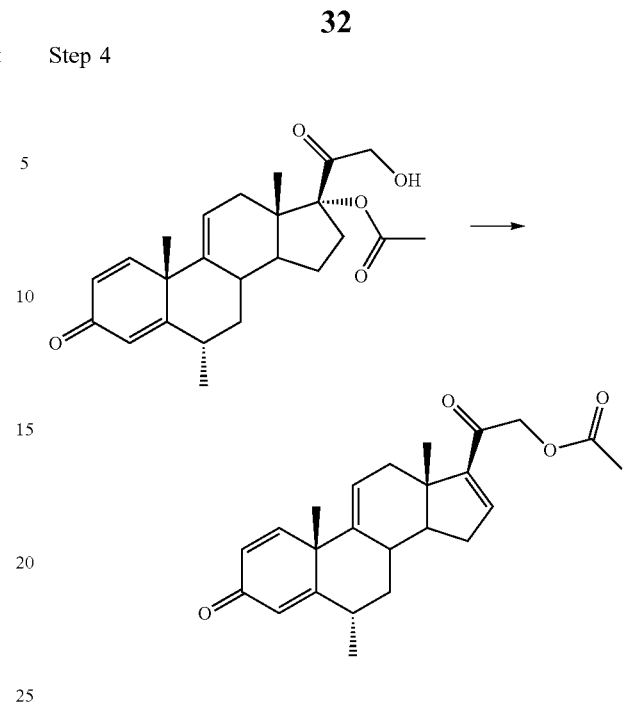

2-oxo-2-(((6S,10R,13S)-6,10,13-trimethyl-3-oxo-6,7,8,10,12,13,14,15-octahydro-3H-cyclopenta[a]phenanthren-17-yl)ethyl acetate: (6S,10R,13S)-17-(2-hydroxyacetyl)-6,10,13-trimethyl-3-oxo-6,7,8,10,12,13,14,15,16,17-decahydro-3H-cyclopenta[a]phenanthren-1'7-yl acetate is heated with 2 equivalents of potassium carbonate in dimethyl formamide. Standard aqueous workup yields the title compound.

EXAMPLE 1

(10S,13S,17R)-17-hydroxy-17-(2-hydroxyacetyl)-10,13-dimethyl-6,7,8,10,12,13,14,15,16,17-decahydro-1H-cyclopenta[a]phenanthren-3(2H)-one

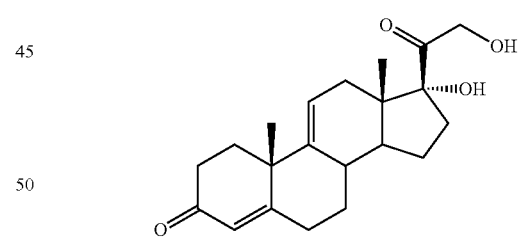

Step 1

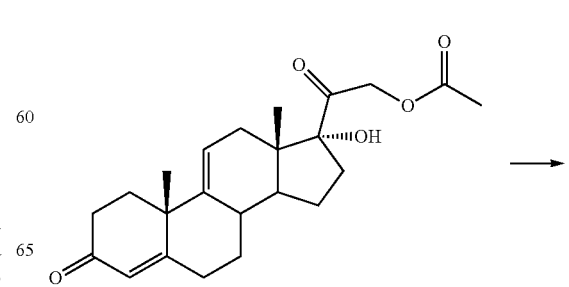

33
-continued

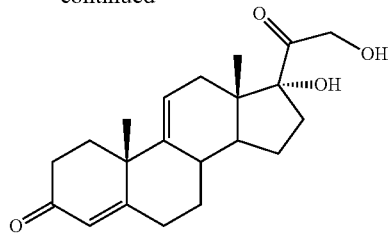

(10S,13S,17R)-17-hydroxy-17-(2-hydroxyacetyl)-10,13-dimethyl-6,7,8,10,12,13,14,15,16,17-decahydro-1H-cyclopenta[a]phenanthren-3(2H)-one: Commercially available as Anecortave acetate. The title compound can be synthesized according to the procedure of Example 8, Step 2, substituting 2-((10S,13S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl acetate for 2-oxo-2-((10S,13S,16R,17S)-10,13,16-trimethyl-3-oxo-2,3,6,7,8,10,12,13,14,15,16,17-dodecahydro-1H-cyclopenta[a]phenanthren-17-yl)ethyl acetate.

EXAMPLE 2

(10S,13S,17R)-17-hydroxy-17-(2-hydroxyacetyl)-10,13-dimethyl-6,7,8,10,12,13,14,15,16,17-decahydro-3H-cyclopenta[a]phenanthren-3-one

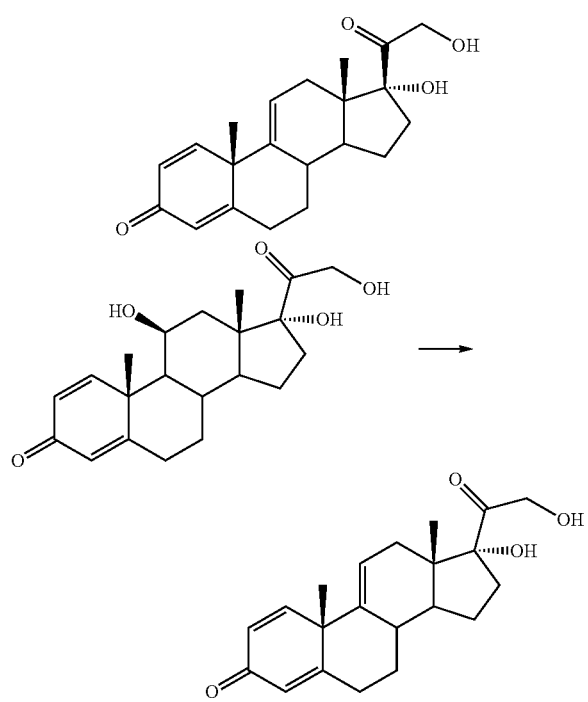

(10S,13S,17R)-17-hydroxy-17-(2-hydroxyacetyl)-10,13-dimethyl-6,7,8,10,12,13,14,15,16,17-decahydro-3H-cyclopenta[a]phenanthren-3-one: The title compound can be synthesized according to the procedures of Example 3, Step 1 and Example 1, Step 1, substituting prednisolone acetate for hydrocortisone acetate.

34

EXAMPLE 3

2-((10S,13S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl acetate

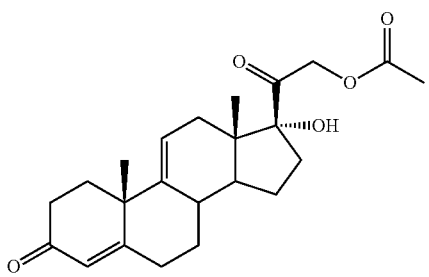 [SMILES: CC(=O)OCC(=O)[C@@]1(O)CCC2C3CCC4=CC(=O)CC[C@]4(C)C3=CC[C@@]21C]

Step 1

2-((10S,13S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl acetate: The title compound can be synthesized from hydrocortisone acetate according to the procedure disclosed in EP 0097328. 405 g (1 mol) of hydrocortisone acetate is added to a mixture of 2 liters of N,N-dimethylformamide and 350 ml of pyridine, and with stirring at room temperature, 260 g of methanesulfonyl chloride is added. The reaction mixture is heated, maintained at 80 to 85° c. for 1 hour, and then cooled to room temperature. Methanol (7 liters) is added. The precipitated crystals are separated by filtration, washed with methanol and water, and dried under reduced pressure to give the title compound.

EXAMPLE 6

(10S,13S,16R,17S)-17-(2-hydroxyacetyl)-10,13,16-trimethyl-6,7,8,10,12,13,14,15,16,17-decahydro-3H-cyclopenta[a]phenanthren-3-one

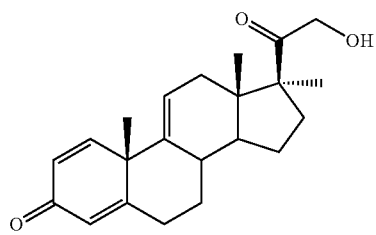 [SMILES: C[C@]12C=CC(=O)C=C1CCC1C2=CC[C@@]2(C)C1CC[C@]2(C)C(=O)CO]

Step 1

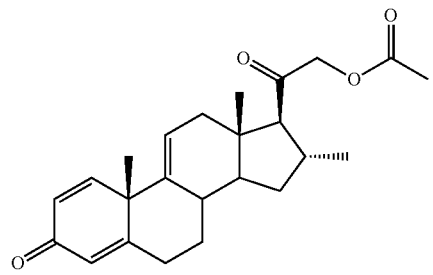

(10S,13S,16R,17S)-17-(2-hydroxyacetyl)-10,13,16-trimethyl-6,7,8,10,12,13,14,15,16,17-decahydro-3H-cyclopenta[a]phenanthren-3-one: A solution of the product from Example 7, step 2 in methylene chloride and methanol (1:3 methylene chloride/methanol) is stirred under an inert atmosphere and cooled in an ice bath. Aqueous potassium carbonate is added by syringe. The reaction is stirred at 5° C. for 2 hours. The reaction is then neutralized with 1N HCl and concentrated. After partitioning between water and methylene chloride, the product solution is dried over anhydrous magnesium sulfate, filtered and evaporated to give the title compound.

EXAMPLE 7

2-oxo-2-((10S,13S,16R)-10,13,16-trimethyl-3-oxo-6,7,8,10,12,13,14,15,16,17-decahydro-3H-cyclopenta[a]phenanthren-17-yl)ethyl acetate

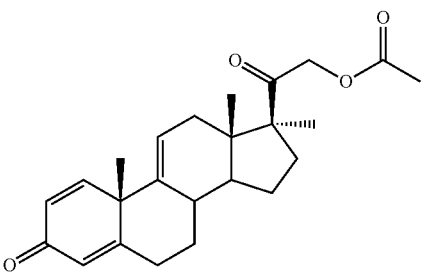 [SMILES: CC(=O)OCC(=O)[C@@]1(C)CCC2C3CCC4=CC(=O)C=C[C@]4(C)C3=CC[C@@]21C]

Step 1

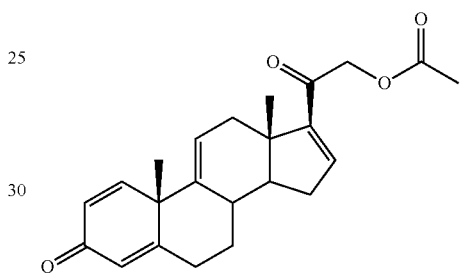

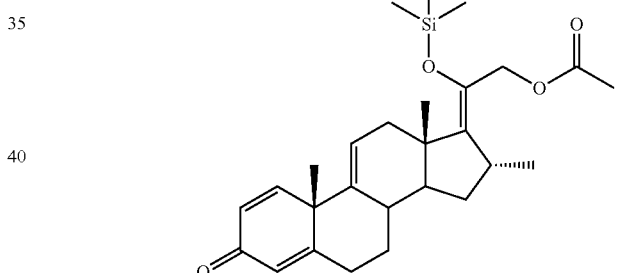

2-((10S,13S,16R)-10,13,16-trimethyl-3-oxo-7,8,12,13,15,16-hexahydro-3H-cyclopenta[a]phenanthren-17(6H,10H,14H)-ylidene)-2-(trimethylsilyloxy)ethyl acetate: (see K. P. Shephard, U.S. Pat. No. 4,975,536; Dec. 4, 1990; Preparation 1, col. 8) Into predried reactor 1 was added 36.64 grams (100 mmole) of 2-((10S,13S)-10,13-dimethyl-3-oxo-6,7,8,10,12,13,14,15-octahydro-3H-cyclopenta[a]phenanthren-17-yl)-2-oxoethyl acetate (commercial product from Pfizer). The starting material was dissolved in 200 ml of anhydrous tetrahydrofuran and 200 ml of anhydrous dichloromethane. Trimethylsilyl imidazole, (20.0 ml, 136 mmole), was added. This solution was cooled to −50° C. under a small nitrogen flow.

Into predried reactor 2 was added copper II propionate (2.10 grams, 10.0 mmole), 150 ml of anhydrous tetrahydrofuran, and anhydrous 1,3-dimethyl-3,4,5,6-tetrahydro-2(1H)-pyrimidinone. The mixture was cooled to −50° C. and methyl magnesium chloride (3M, 10.0 ml) was added dropwise over approximately 5 minutes. The mixture was stirred for approximately 10 minutes. The contents of reactor 2 were transferred to reactor 1 via cannula quickly (approximately 30 sec.), and reactor 2 was rinsed with 10 ml of anhydrous tetrahydrofuran and this was also cannulated into reactor 1. A pump was set up with methyl magnesium chloride (3M, 45.0 ml) and pumped into reactor 1 over 45 min (pump setting at 1.0 ml/min). Reactor 1 was stirred further at −50° C. for 1 hour, then warmed to −30° C. overnight.

Toluene (1 L) was added and the temperature brought to 0° C. The mixture was extracted with 2×500 ml of 5% acetic acid (cold), then with 200 ml of 25% sodium chloride. The aqueous phases were back extracted with 300 ml of toluene. The combined toluene extracts were dried over magnesium sulfate, filtered, and concentrated to a viscous oil. Yield—57.8 grams.

Step 2

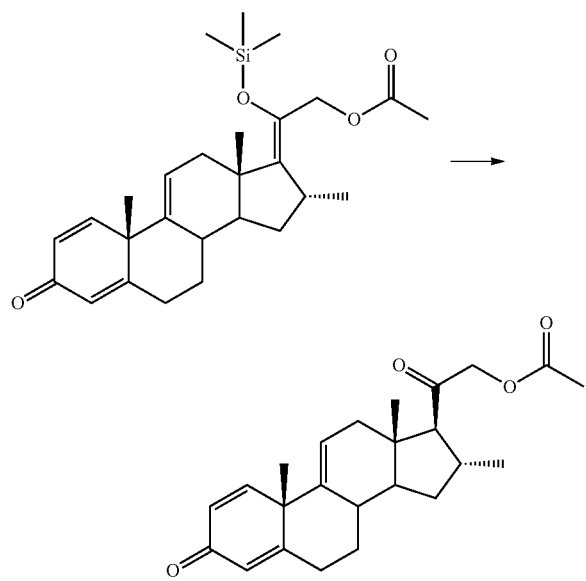

2-oxo-2-((10S,13S,16R,17S)-10,13,16-trimethyl-3-oxo-6,7,8,10,12,13,14,15,16,17-decahydro-3H-cyclopenta[a]phenanthren-17-yl)ethyl acetate: The crude product from step 1 is dissolved in ethyl acetate, and slurried with aqueous 1N HCl until hydrolysis is complete. The aqueous acid is neutralized with aqueous potassium bicarbonate, and the ethyl acetate phase is dried, filtered, and concentrated to a semi-solid.

EXAMPLE 8

(10S,13S,16R,17S)-17-(2-hydroxyacetyl)-10,13,16-trimethyl-6,7,8,10,12,13,14,15,16,17-decahydro-1H-cyclopenta[a]phenanthren-3(2H)-one Step 1

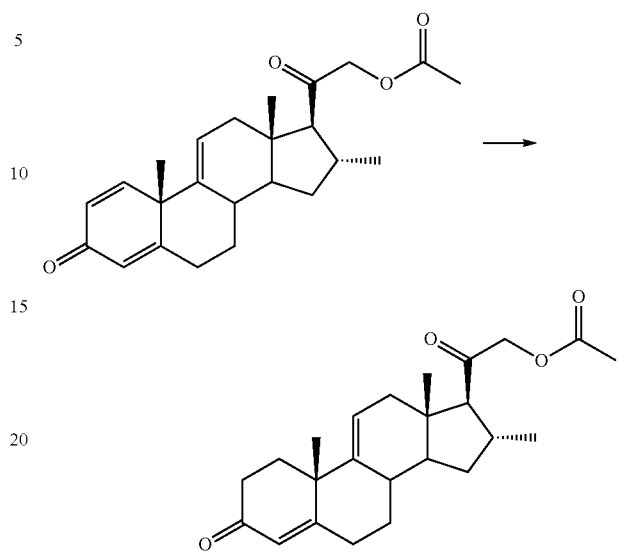

2-oxo-2-((10S,13S,16R,17S)-10,13,16-trimethyl-3-oxo-2,3,6,7,8,10,12,13,14,15,16,17-dodecahydro-1H-cyclopenta[a]phenanthren-17-yl)ethyl acetate: A mixture of 3.3 g (8.6 mM) of 2-oxo-2-((10S,13S,16R,17S)-10,13,16-trimethyl-3-oxo-6,7,8,10,12,13,14,15,16,17-decahydro-3H-cyclopenta[a]phenanthren-17-yl)ethyl acetate, chlorotris(triphenylphosphine)rhodium(I) (Wilkinson's Catalyst, 480 mg, 0.52 mM), triethylsilane (1.4 mL, 1.0 g, 8.8 mM) and methylene chloride (15 mL) was warmed to 40° C. and stirred until most of the starting material was gone, as determined by thin layer chromatography. The reaction was evaporated in vacuo and chromatographed on fine silica gel (600 g) in 10-15% ethyl acetate in methylene chloride. One fraction of 700 mL was collected, followed by twelve 200 mL fractions. A 1.0 g quantity of desired product (30% yield) was obtained by evaporation of fractions 6-12. (Starting material was obtained from fraction 13, 0.7 g, 20% recovery). NMR (500 MHz, CDCl$_3$, TMS): δ 0.68 (s, 3H), 0.98 (d, 3H, J=6.5 Hz), 1.12 (m, 1H), 1.33 (s, 3H), 1.47 (m, 1H), 1.57 (m, 1H), 1.69 (m, 1H), 1.99 (m, 1H), 2.18 (s, 3H), 2.07-2.29 (m, 6H), 2.36 (d, 1H), 2.50 (m, 3H), 2.79 (m, 1H), 4.48 (d, 1H, J=17 Hz), 4.73 (d, 1H, J=17 Hz), 5.50 (s, 1H), 5.75 (s, 1H).

Step 2

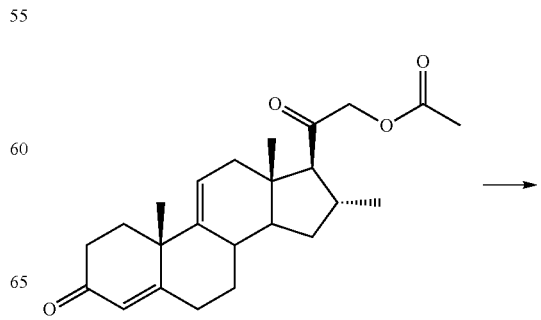

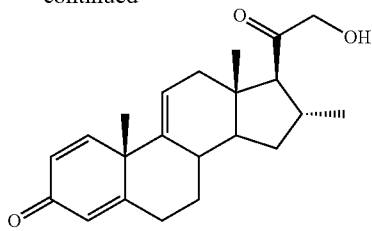

(10S,13S,16R,17S)-17-(2-hydroxyacetyl)-10,13,16-trimethyl-6,7,8,10,12,13,14,15,16,17-decahydro-3H-cyclopenta[a]phenanthren-3-one: A solution of 2-oxo-2-((10S,13S,16R,17S)-10,13,16-trimethyl-3-oxo-2,3,6,7,8,10,12,13,14,15,16,17-dodecahydro-1H-cyclopenta[a]phenanthren-17-yl)ethyl acetate (1.0 g, 2.6 mM) in methylene chloride (5 mL) and methanol (15 mL) was put under an inert atmosphere and cooled in an ice bath. 1 mL of 1 M aqueous potassium carbonate was added by syringe. The reaction was stirred at 5° C. for 2 h. The reaction was then neutralized with 1N HCl and concentrated. After partitioning between water and methylene chloride, the product solution was dried over anhydrous magnesium sulfate, filtered and evaporated. Crystallization from ethyl acetate yielded a first crop of 0.33 g product. NMR (500 MHz, CDCl$_3$, TMS): δ 0.67 (s, 3H), 1.01 (d, 3H, J=7 Hz), 1.13 (m, 1H), 1.33 (s, 3H), 1.47-1.80 (m, 3, H), 2.00 (m, 1H), 2.06-2.24 (m, 6H), 2.37 (d, 1H), 2.45-2.60 (m, 3H), 2.82 (m, 1H), 3.30 (m, 1H), 4.20 (m, 2H), 5.50 (d, 1H, J=5 Hz), 5.76 (s, 1H).

EXAMPLE 15

(10S,13S,16R,17R)-17-hydroxy-17-(2-hydroxyacetyl)-10,13,16-trimethyl-6,7,8,10,12,13,14,15,16,17-decahydro-3H-cyclopenta[a]phenanthren-3-one

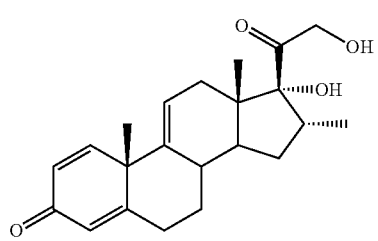 [SMILES: C[C@@H]1CC2C3CCC4=CC(=O)C=C[C@]4(C)C3=CC[C@]2(C)[C@@]1(O)C(=O)CO]

Step 1

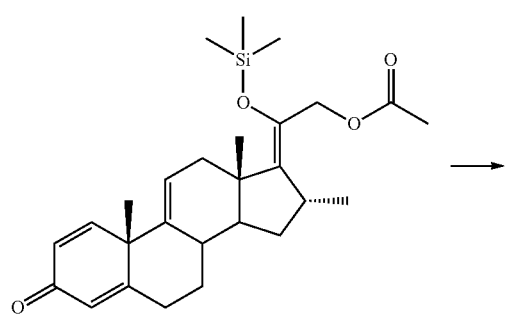

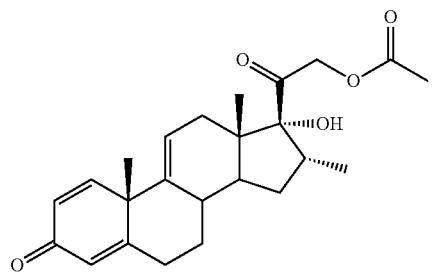

2-((10S,13S,16R,17R)-17-hydroxy-10,13,16-trimethyl-3-oxo-6,7,8,10,12,13,14,15,16,17-decahydro-3H-cyclopenta[a]phenanthren-17-yl)-2-oxoethyl acetate: (Z)-2-((10S,13S,16R)-10,13,16-trimethyl-3-oxo-7,8,12,13,15,16-hexahydro-3H-cyclopenta[a]phenanthren-17(6H,10H,14H)-ylidene)-2-(trimethylsilyloxy)ethyl acetate is dissolved in methylene chloride and the mixture is cooled to zero degrees Celsius. A solution of m-chloroperbenzoic acid in methylene chloride is added dropwise and the mixture is stirred for 4 hours. The organic phase was washed with aqueous acetic acid and then aqueous bisulfite. The organic phase was concentrated and chromatographed on silica gel to yield the title compound.

Step 2

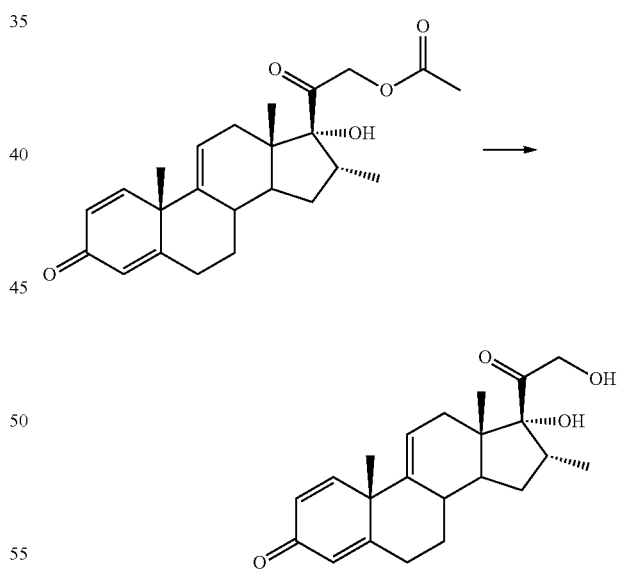

(10S,13S,16R,17R)-17-hydroxy-17-(2-hydroxyacetyl)-10,13,16-trimethyl-6,7,8,10,12,13,14,15,16,17-decahydro-3H-cyclopenta[a]phenanthren-3-one: Prepared according to Example 8, Step 2 substituting 2-((10S,13S,16R,17R)-17-hydroxy-10,13,16-trimethyl-3-oxo-6,7,8,10,12,13,14,15,16,17-decahydro-3H-cyclopenta[a]phenanthren-17-yl)-2-oxoethyl acetate for 2-oxo-2-((10S,13S,16R,17S)-10,13,16-trimethyl-3-oxo-2,3,6,7,8,10,12,13,14,15,16,17-dodecahydro-1H-cyclopenta[a]phenanthren-17-yl)ethyl acetate.

EXAMPLE 16

(10S,13S,16S,17R)-17-hydroxy-17-(2-hydroxy-acetyl)-10,13,16-trimethyl-6,7,8,10,12,13,14,15,16,17-decahydro-3H-cyclopenta[a]phenanthren-3-one

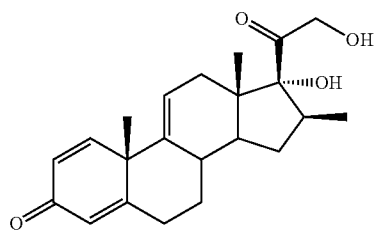 [SMILES: C[C@H]1CC2C3CCC4=CC(=O)C=C[C@]4(C)C3=CC[C@]2(C)[C@@]1(O)C(=O)CO]

EXAMPLE 19

(10S,13S,16R,17R)-17-hydroxy-17-(2-hydroxy-acetyl)-10,13,16-trimethyl-6,7,8,10,12,13,14,15,16,17-decahydro-1H-cyclopenta[a]phenanthren-3(2H)-one

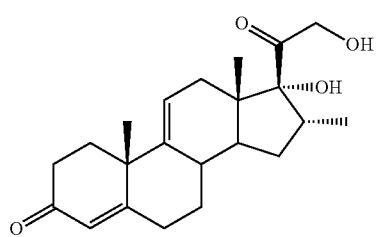 [SMILES: C[C@@H]1CC2C3CCC4=CC(=O)CC[C@]4(C)C3=CC[C@]2(C)[C@@]1(O)C(=O)CO]

EXAMPLE 20

(10S,13S,16S,17R)-17-hydroxy-17-(2-hydroxy-acetyl)-10,13,16-trimethyl-6,7,8,10,12,13,14,15,16,17-decahydro-1H-cyclopenta[a]phenanthren-3(2H)-one

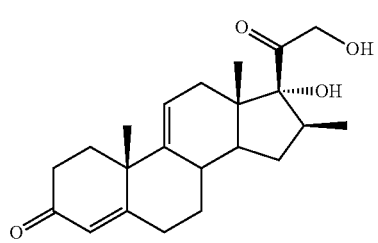 [SMILES: C[C@H]1CC2C3CCC4=CC(=O)CC[C@]4(C)C3=CC[C@]2(C)[C@@]1(O)C(=O)CO]

EXAMPLE 21

(10S,13S,16R,17R)-17-hydroxy-17-(2-hydroxy-acetyl)-10,13-dimethyl-16-propyl-6,7,8,10,12,13,14,15,16,17-decahydro-1H-cyclopenta[a]phenanthren-3(2H)-one

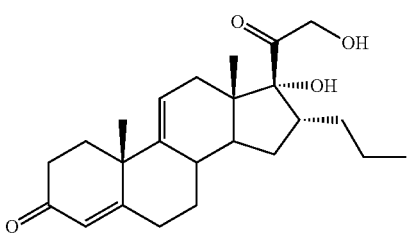 [SMILES: CCC[C@@H]1CC2C3CCC4=CC(=O)CC[C@]4(C)C3=CC[C@]2(C)[C@@]1(O)C(=O)CO]

EXAMPLE 22

(10S,13S,16R,17R)-17-hydroxy-17-(2-hydroxy-acetyl)-10,13-dimethyl-16-propyl-6,7,8,10,12,13,14,15,16,17-decahydro-3H-cyclopenta[a]phenanthren-3-one

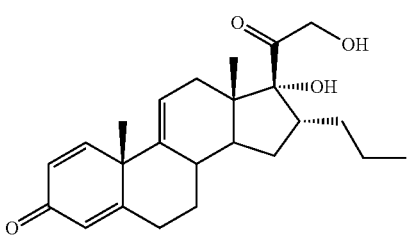 [SMILES: CCC[C@@H]1CC2C3CCC4=CC(=O)C=C[C@]4(C)C3=CC[C@]2(C)[C@@]1(O)C(=O)CO]

EXAMPLE 23

(10S,13S,16R,17S)-17-(2-hydroxyacetyl)-10,13-dimethyl-16-propyl-6,7,8,10,12,13,14,15,16,17-decahydro-3H-cyclopenta[a]phenanthren-3-one

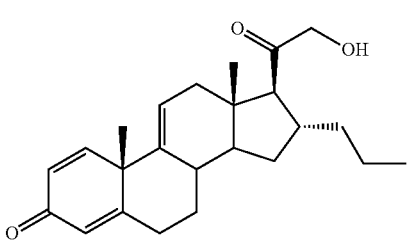 [SMILES: CCC[C@@H]1CC2C3CCC4=CC(=O)C=C[C@]4(C)C3=CC[C@]2(C)[C@H]1C(=O)CO]

EXAMPLE 24

(10S,13S,16R,17S)-17-(2-hydroxyacetyl)-10,13-dimethyl-16-propyl-6,7,8,10,12,13,14,15,16,17-decahydro-1H-cyclopenta[a]phenanthren-3(2H)-one

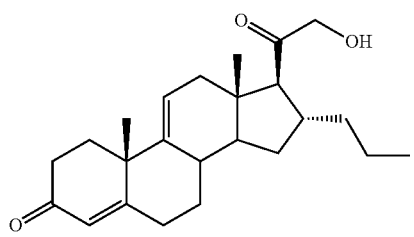 [SMILES: CCC[C@@H]1CC2C3CCC4=CC(=O)CC[C@]4(C)C3=CC[C@]2(C)[C@H]1C(=O)CO]

EXAMPLE 25

(10S,13S,16R,17S)-17-(2-hydroxyacetyl)-10,13-dimethyl-16-phenyl-6,7,8,10,12,13,14,15,16,17-decahydro-1H-cyclopenta[a]phenanthren-3(2H)-one

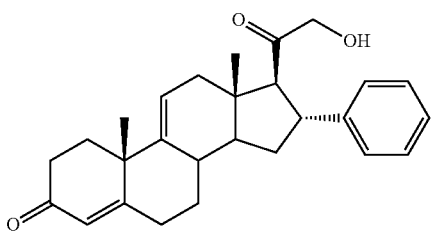 [SMILES: C[C@]12CCC(=O)C=C1CCC1C2=CC[C@@]2(C)C1C[C@@H](c1ccccc1)[C@@H]2C(=O)CO]

EXAMPLE 26

(10S,13S,16S,17R)-17-hydroxy-17-(2-hydroxyacetyl)-10,13-dimethyl-16-phenyl-6,7,8,10,12,13,14,15,16,17-decahydro-1H-cyclopenta[a]phenanthren-3(2H)-one

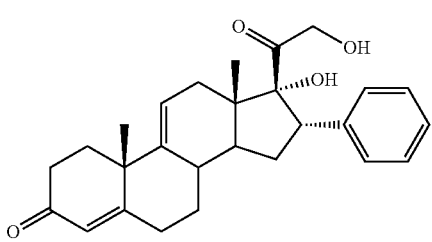 [SMILES: C[C@]12CCC(=O)C=C1CCC1C2=CC[C@@]2(C)C1C[C@@H](c1ccccc1)[C@]2(O)C(=O)CO]

EXAMPLE 27

(10S,13S,16S,17R)-17-hydroxy-17-(2-hydroxyacetyl)-10,13-dimethyl-16-phenyl-6,7,8,10,12,13,14,15,16,17-decahydro-3H-cyclopenta[a]phenanthren-3-one

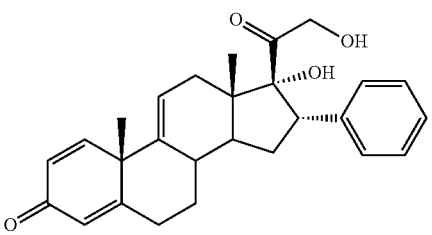 [SMILES: C[C@]12C=CC(=O)C=C1CCC1C2=CC[C@@]2(C)C1C[C@@H](c1ccccc1)[C@]2(O)C(=O)CO]

EXAMPLE 28

(10S,13S,16R,17S)-17-(2-hydroxyacetyl)-10,13-dimethyl-16-phenyl-6,7,8,10,12,13,14,15,16,17-decahydro-3H-cyclopenta[a]phenanthren-3-one

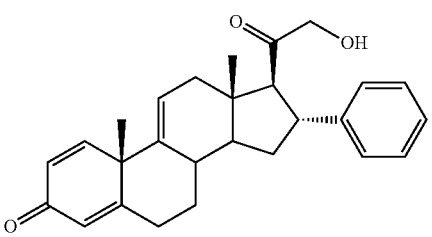 [SMILES: C[C@]12C=CC(=O)C=C1CCC1C2=CC[C@@]2(C)C1C[C@@H](c1ccccc1)[C@@H]2C(=O)CO]

EXAMPLE 29

(10S,13S,16S,17S)-17-(2-hydroxyacetyl)-10,13,16-trimethyl-6,7,8,10,12,13,14,15,16,17-decahydro-3H-cyclopenta[a]phenanthren-3-one

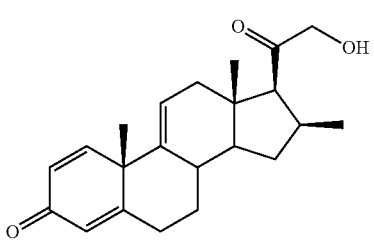 [SMILES: C[C@H]1CC2C3CCC4=CC(=O)C=C[C@]4(C)C3=CC[C@]2(C)[C@H]1C(=O)CO]

EXAMPLE 30

(10S,13S,16S,17S)-17-(2-hydroxyacetyl)-10,13,16-trimethyl-6,7,8,10,12,13,14,15,16,17-decahydro-1H-cyclopenta[a]phenanthren-3(2H)-one

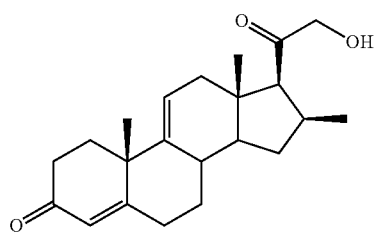 [SMILES: C[C@H]1CC2C3CCC4=CC(=O)CC[C@]4(C)C3=CC[C@]2(C)[C@H]1C(=O)CO]

EXAMPLE 31

2-oxo-2-((10S,13S,16S,17S)-10,13,16-trimethyl-3-oxo-2,3,6,7,8,10,12,13,14,15,16,17-dodecahydro-1H-cyclopenta[a]phenanthren-17-yl)ethyl acetate

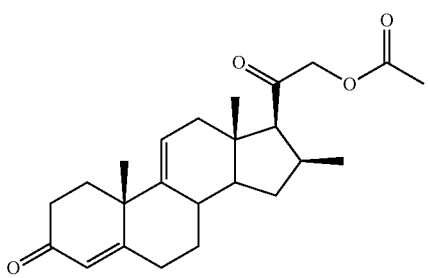 [SMILES: CC(=O)OCC(=O)[C@H]1[C@@H](C)CC2C3CCC4=CC(=O)CC[C@]4(C)C3=CC[C@@]21C]

EXAMPLE 32

(10S,13S,16R,17S)-17-(2-hydroxyacetyl)-10,13,16,17-tetramethyl-6,7,8,10,12,13,14,15,16,17-decahydro-1H-cyclopenta[a]phenanthren-3(2H)-one

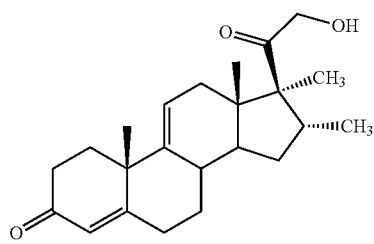 [SMILES: C[C@@H]1CC2C3CCC4=CC(=O)CC[C@]4(C)C3=CC[C@]2(C)[C@@]1(C)C(=O)CO]

Step 1

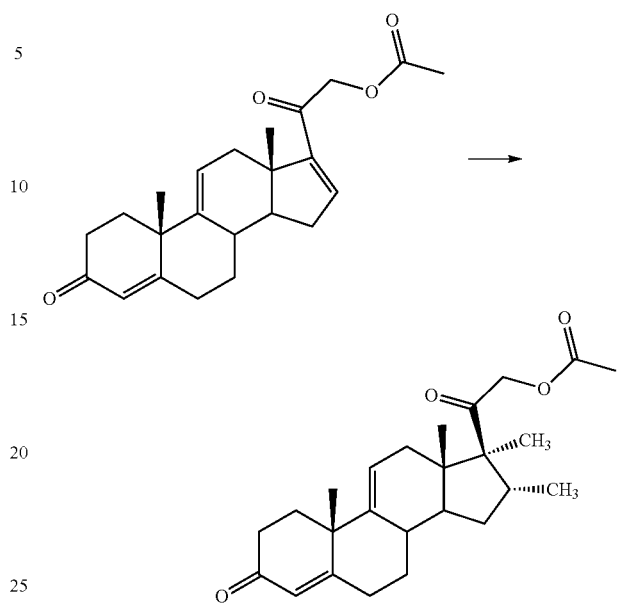

2-oxo-2-((10S,13S,16R,17S)-10,13,16,17-tetramethyl-3-oxo-2,3,6,7,8,10,12,13,14,15,16,17-dodecahydro-1H-cyclopenta[a]phenanthren-17-yl)ethyl acetate: A mixture of 2-((10S,13S)-10,13-dimethyl-3-oxo-2,3,6,7,8,10,12,13,14,15-decahydro-1H-cyclopenta[a]phenanthren-17-yl)-2-oxo-ethyl acetate (150 g) and copper propionate (1.9M in THF (90 ml) is cooled in an ice acetone bath. Methyl magnesium chloride (1.96M in THF, 240 ml) is added dropwise for 30 min. After 1 hour, the reaction is quenched with methyl iodide (100 g) in 200 ml THF. The reaction mixture is then partitioned with water and toluene. The separated organic phase is washed with water, dried over sodium sulfate and concentrated. The residue is crystallized from ether and hexane to give the title compound.

Step 2

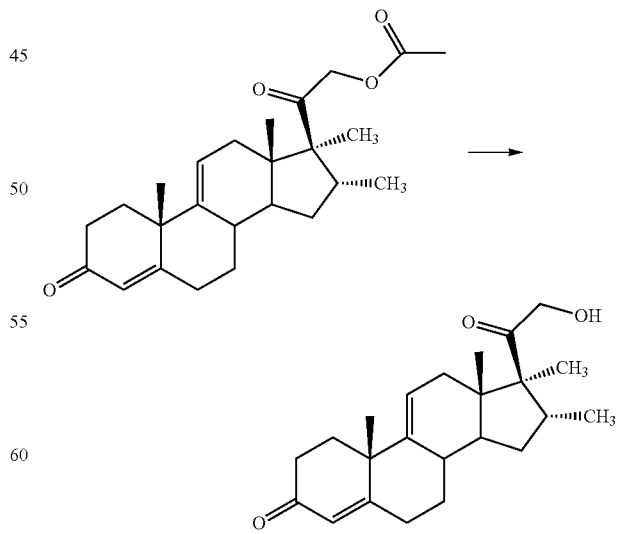

10S,13S,16R,17S)-17-(2-hydroxyacetyl)-10,13,16,17-tetramethyl-6,7,8,10,12,13,14,15,16,17-decahydro-1H-cyclopenta[a]phenanthren-3(2H)-one: 2-oxo-2-((10S,13S,16R, 17S)-10,13,16,17-tetramethyl-3-oxo-2,3,6,7,8,10,12,13,14,15,16,17-dodecahydro-1H-cyclopenta[a]phenanthren-17-yl)ethyl acetate (144 g) is stirred in 1500 ml methanol and treated with sodium methoxide (25%, 5 ml) for 30 minutes. The mixture is partitioned between methylene chloride and sodium bicarbonate. The organic phase is separated and washed with sodium bicarbonate, dried over sodium sulfate, and concentrated to give the title compound.

The following compounds can generally be made using the methods described above. It is expected that these compounds when made will have activity similar to those that have been made and tested.

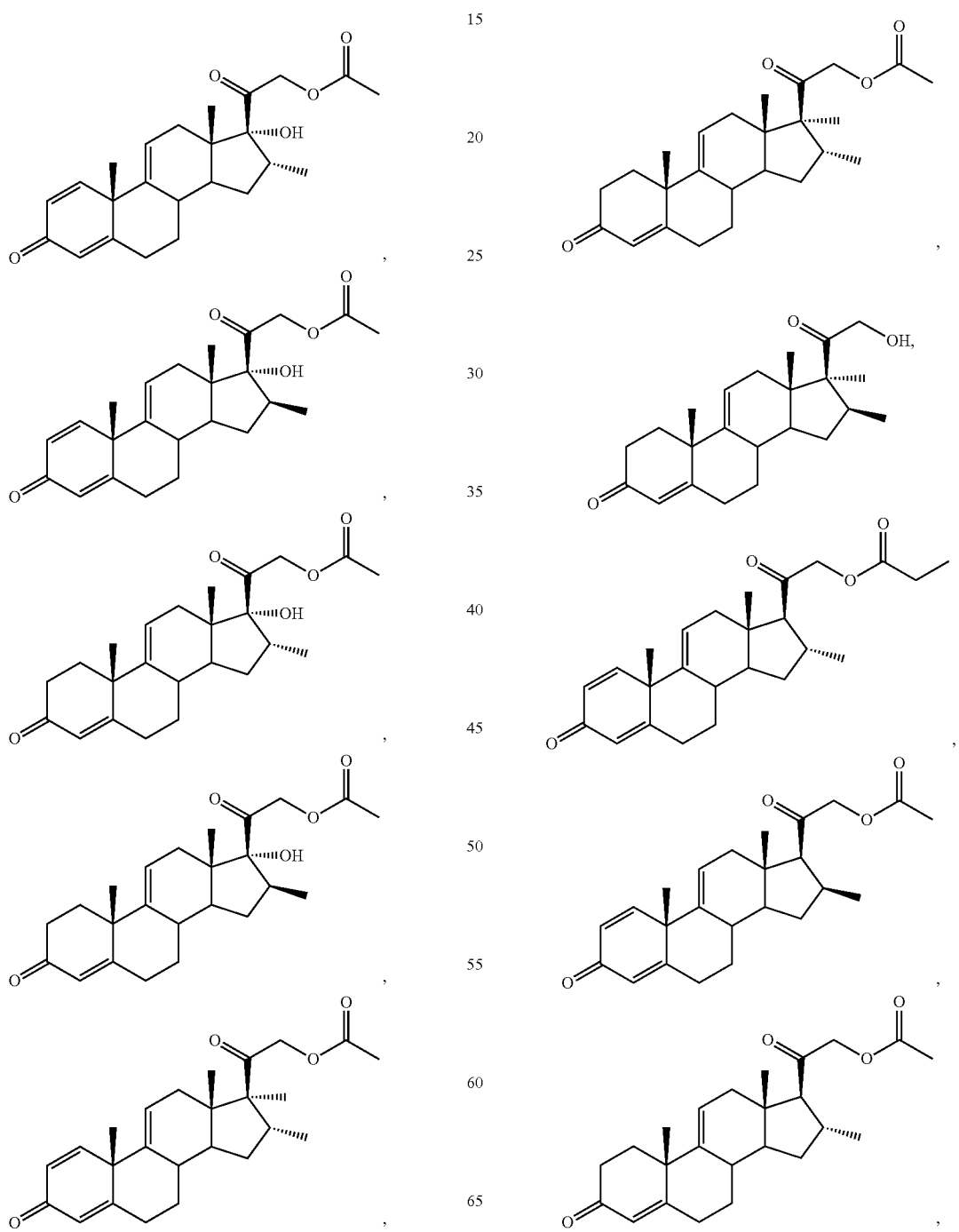

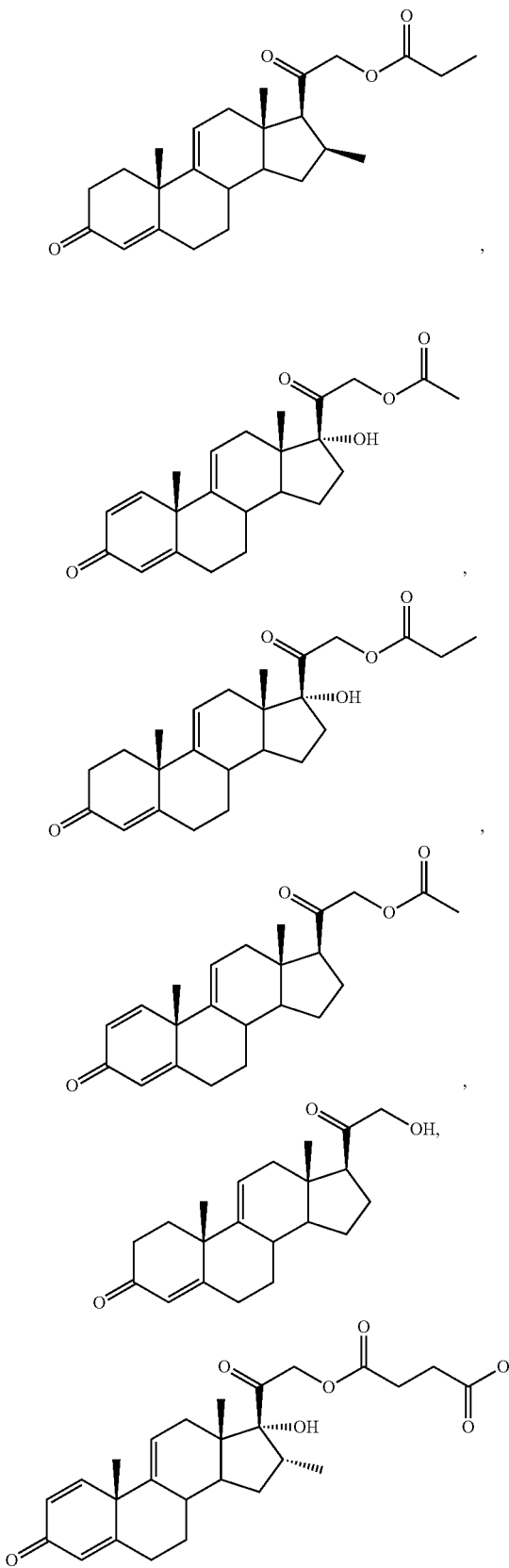
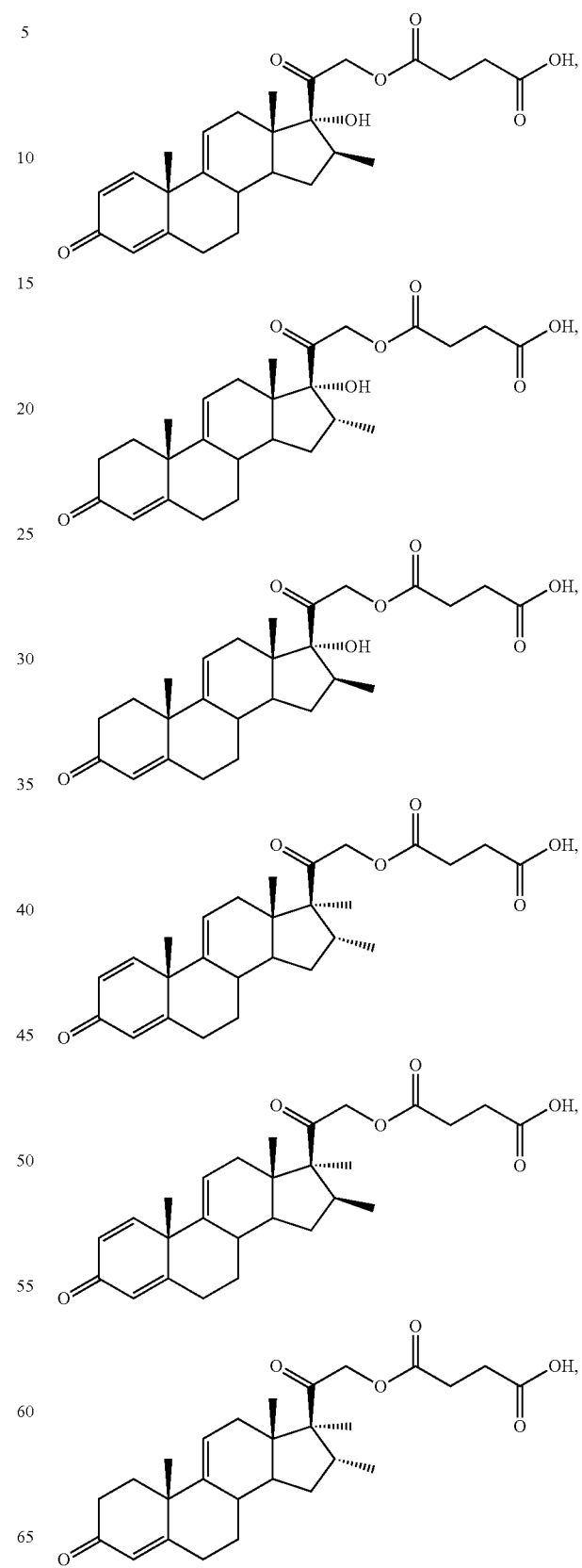

51
-continued
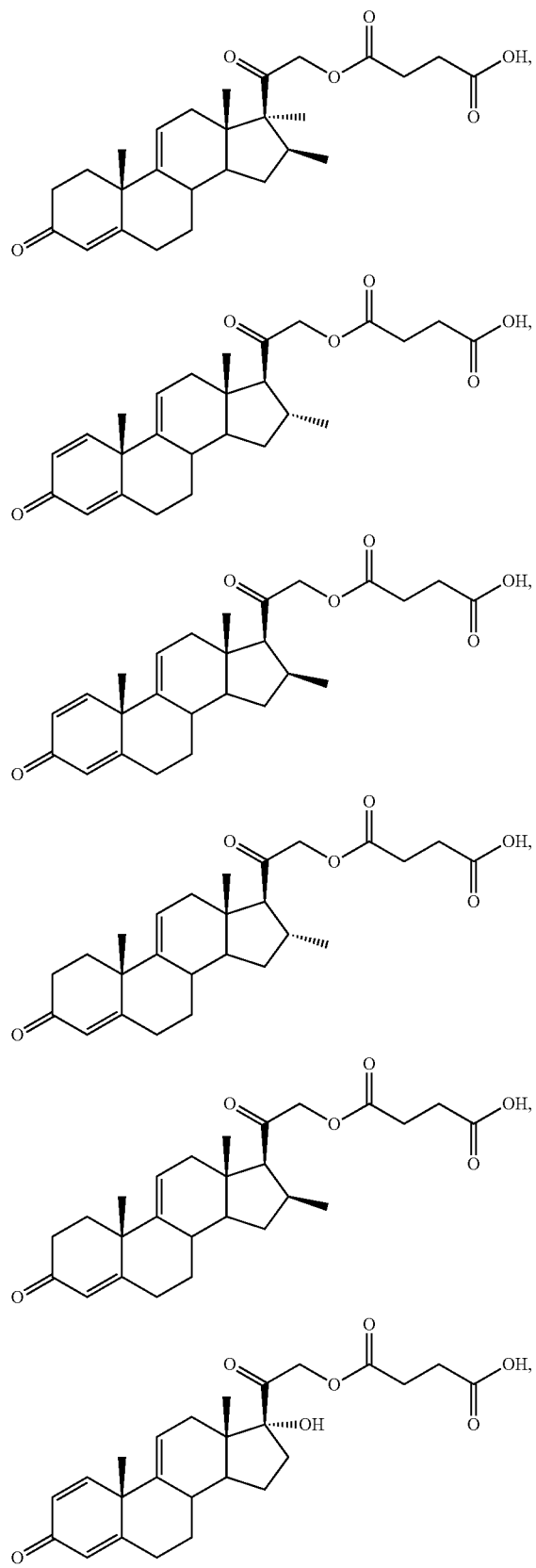
52
-continued
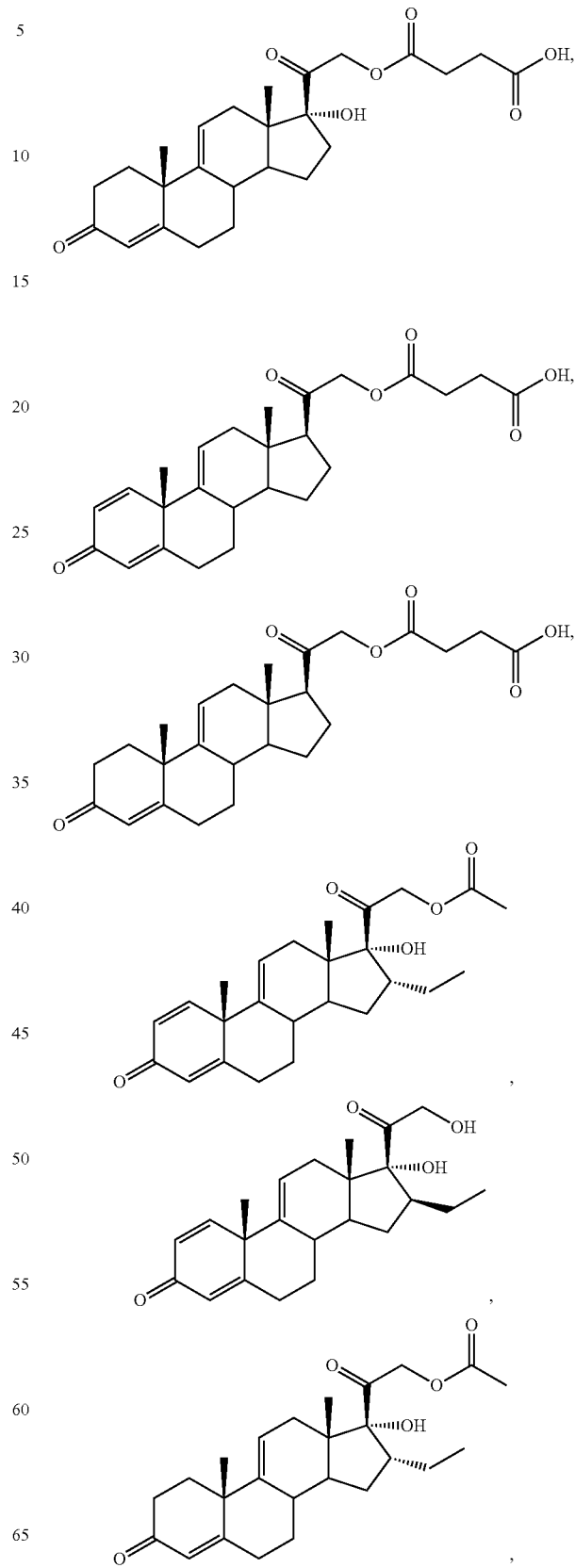

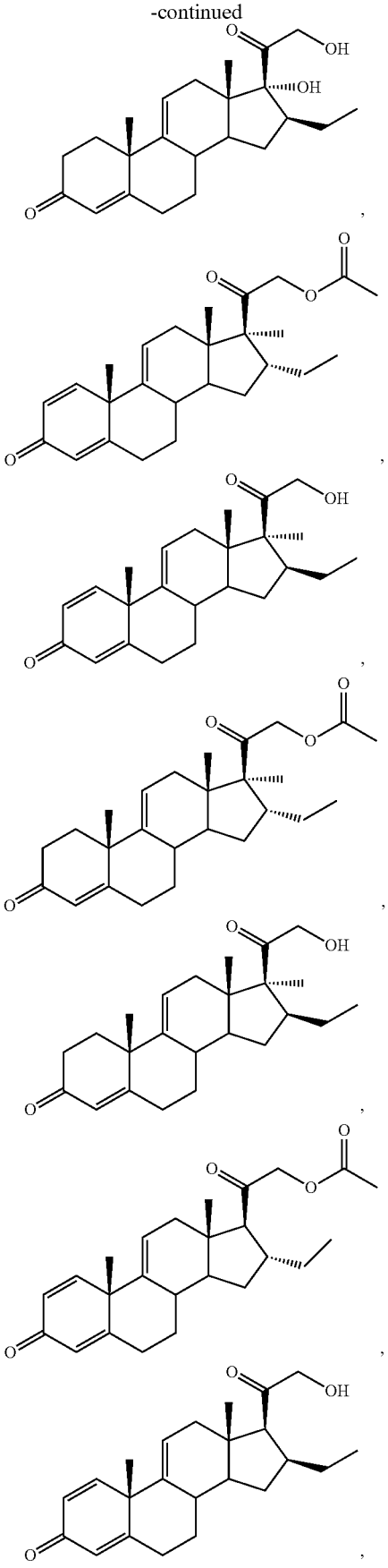
,
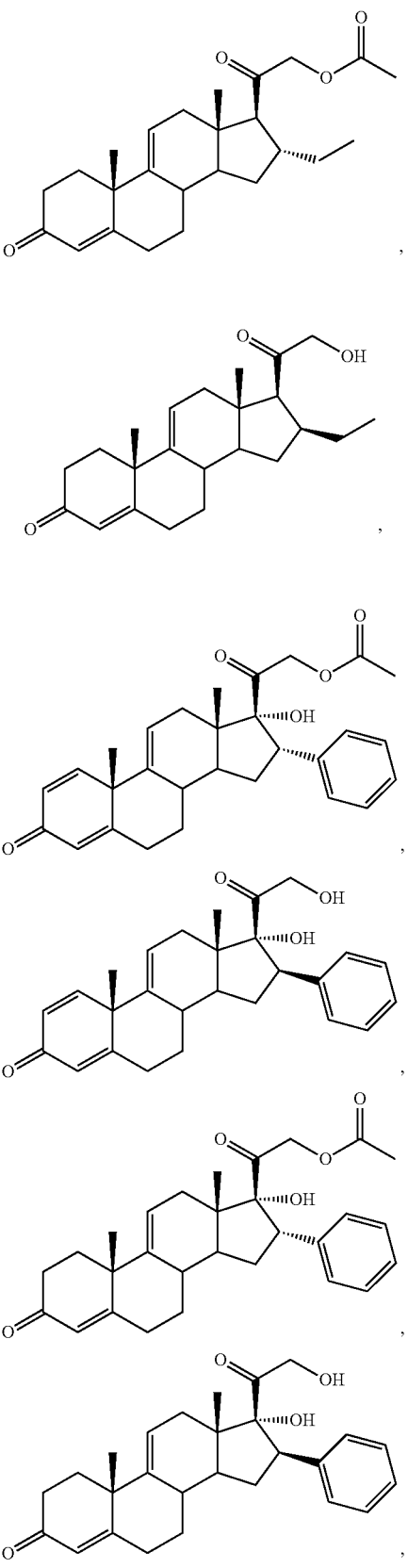
,

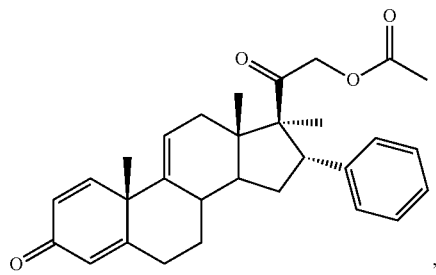
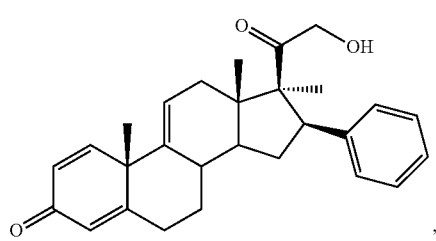
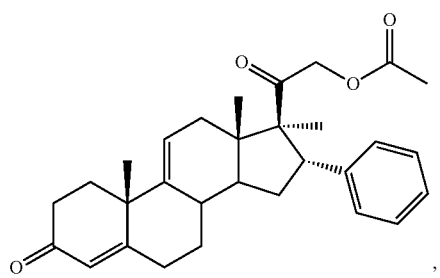
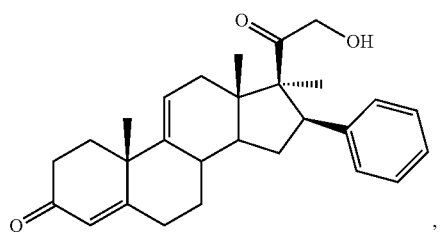
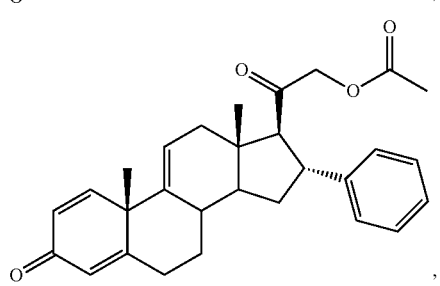
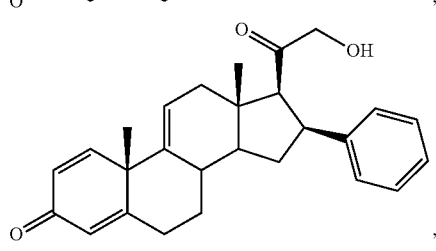
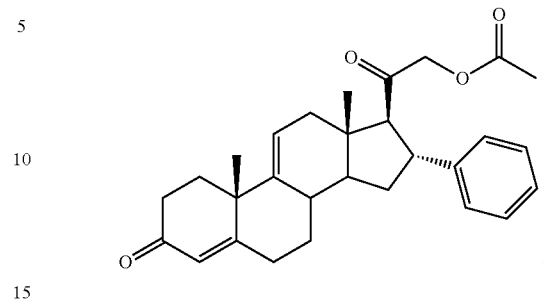
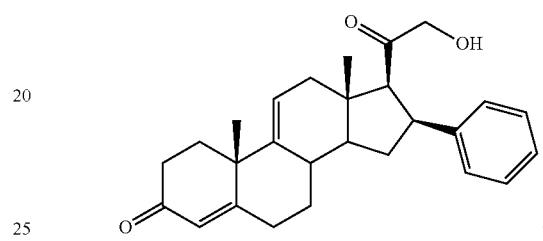
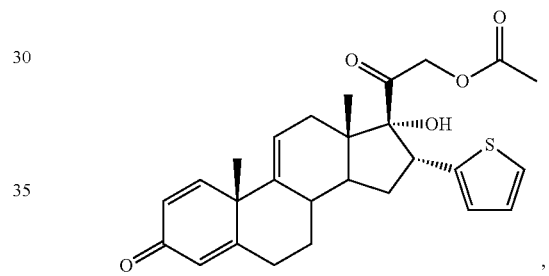
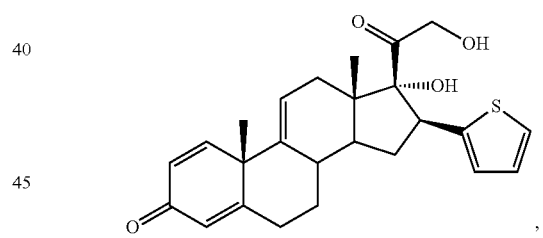
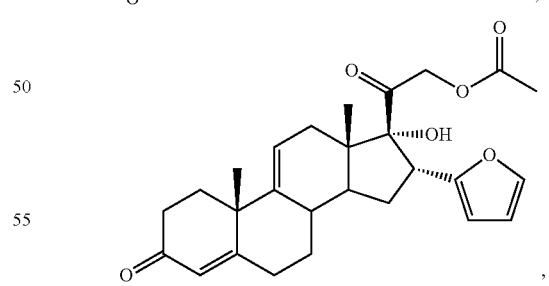
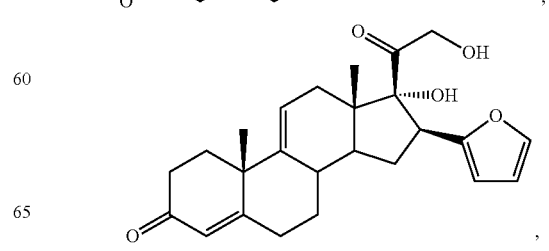

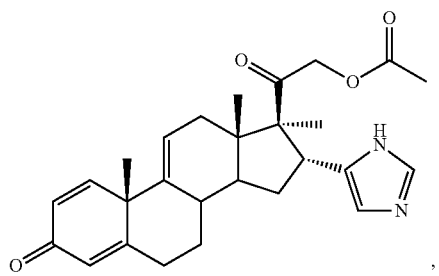
,
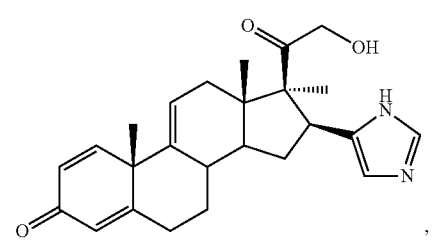
,
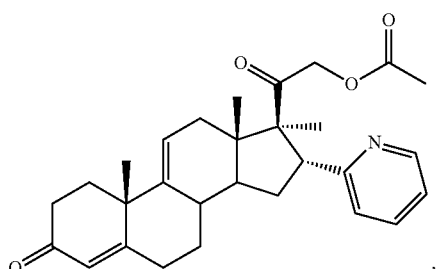
,
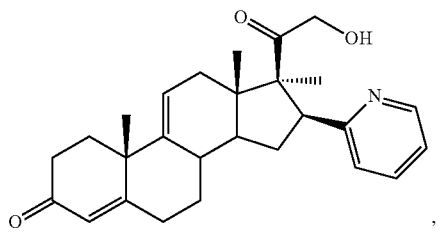
,
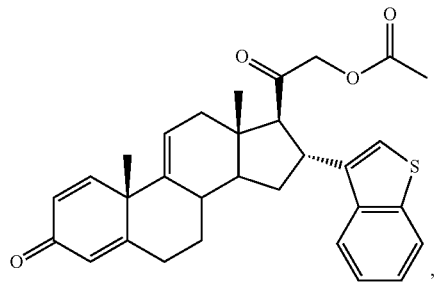
,
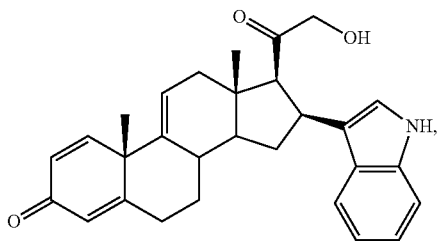
,
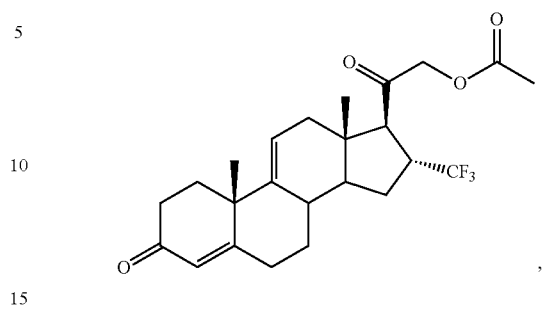
,
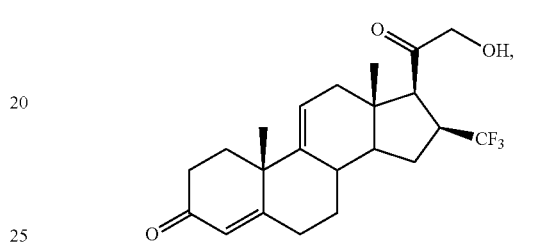
,
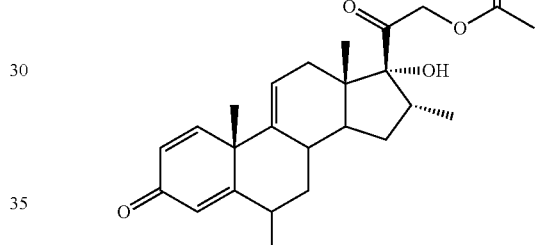
,
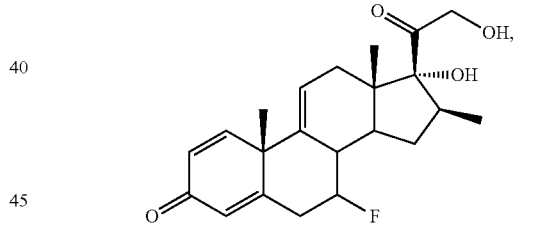
,
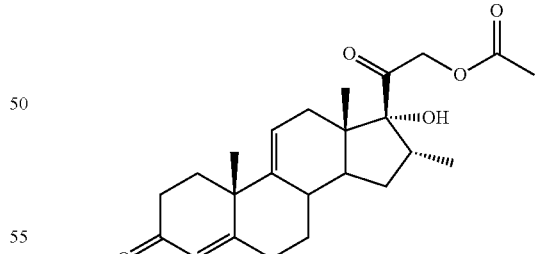
,
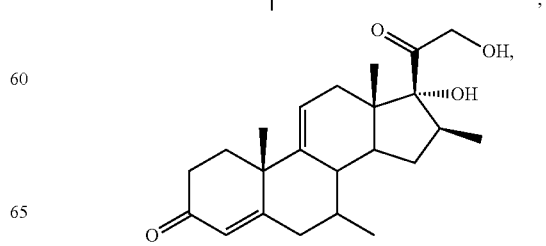
,

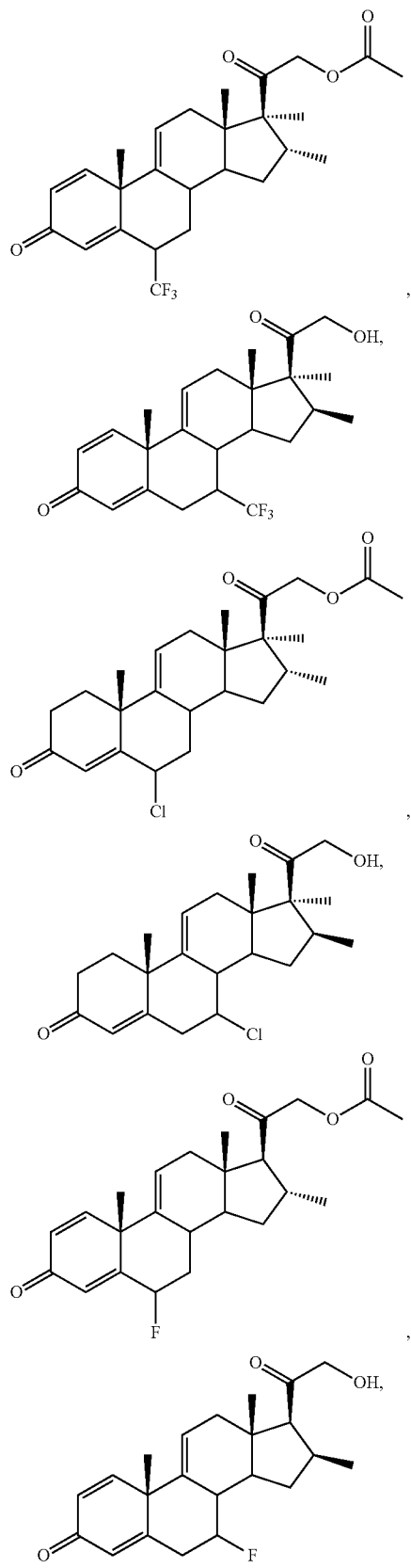
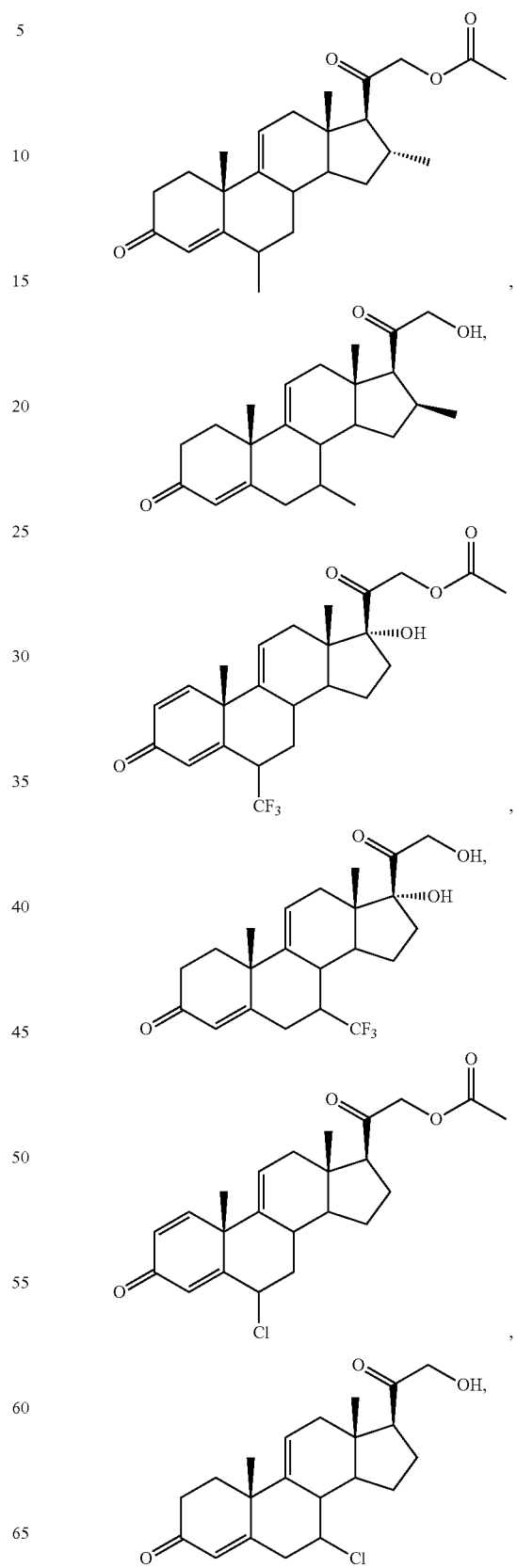

-continued
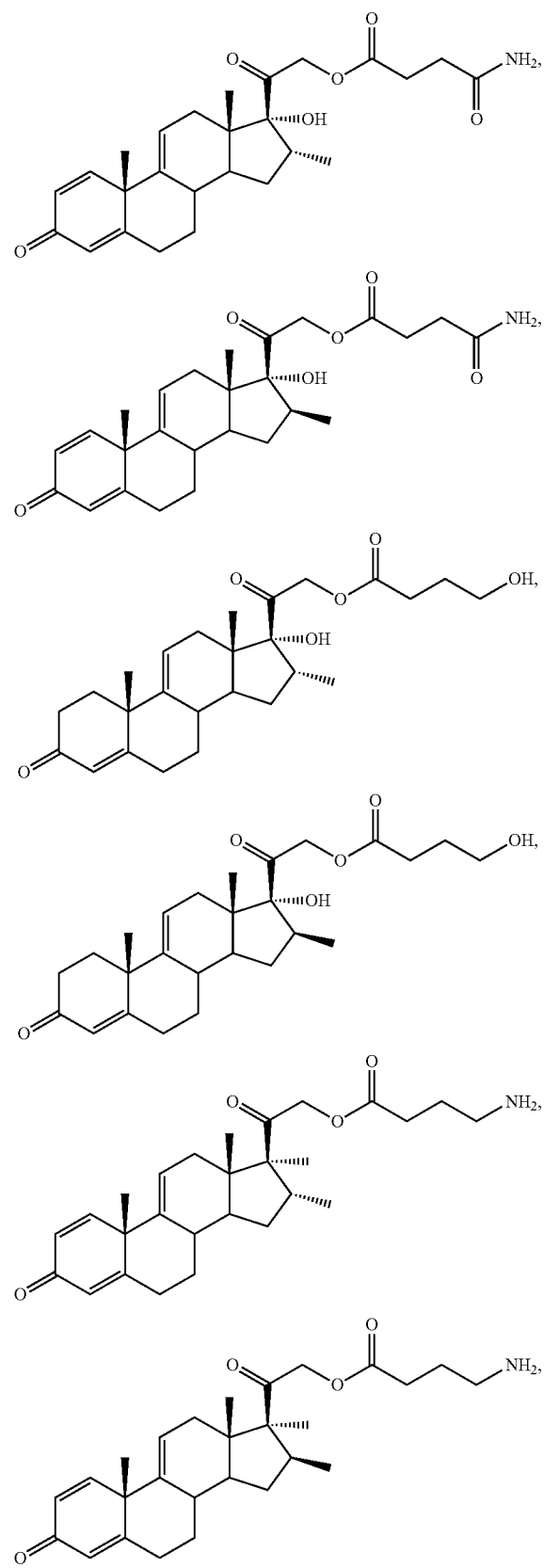
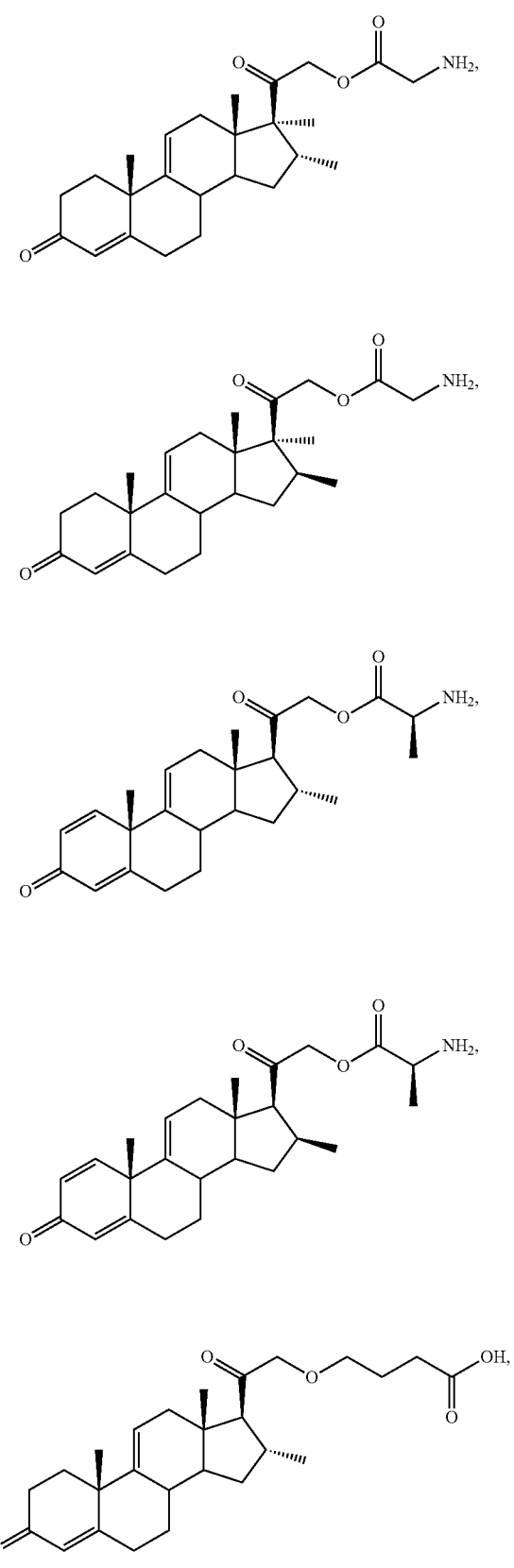

-continued

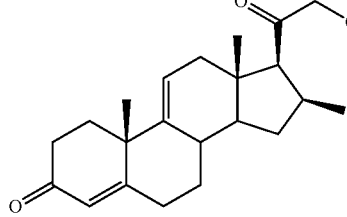

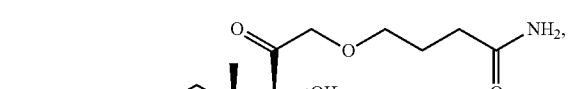

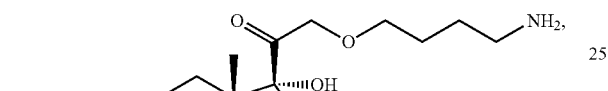

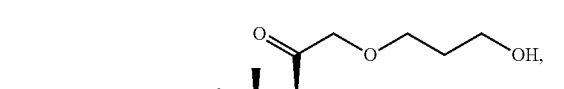

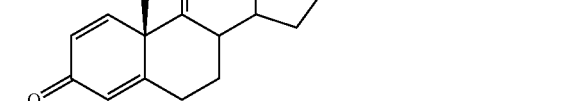

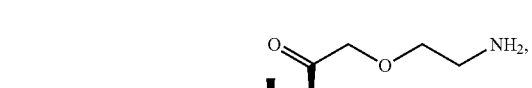

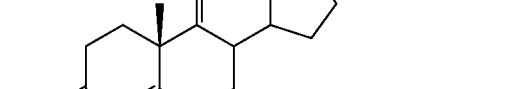

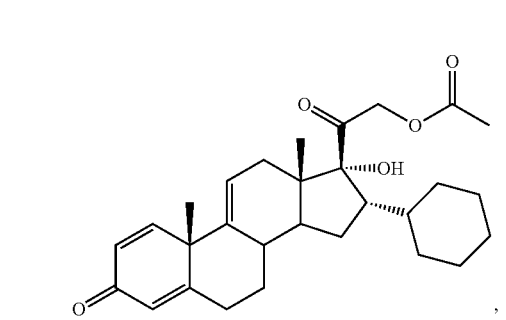

-continued

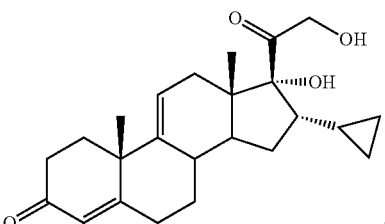

,

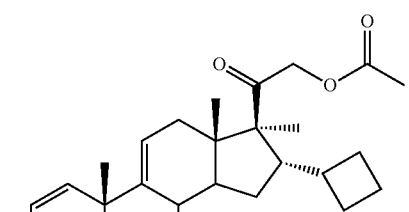

,

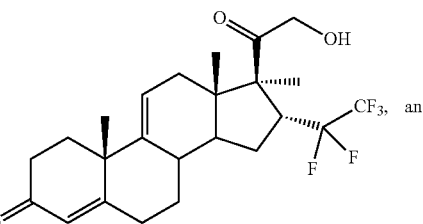

and

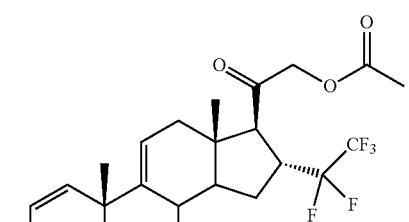

.

The activity of the compounds in Examples 1-7 and 15-16 as NF-κB modulators is illustrated in the following assays. The other compounds listed above, which have not yet been made and/or tested, are predicted to have activity in these assays as well.

Biological Activity Assay

In Vitro NF-kB Inhibitor Screening Assay

C2C12 skeletal muscle cells stably tranfected with a luciferase reporter construct regulated under multiple copies of the NF-kB response element (Panomics, Fremont, CA) were used to screen NF-kB inhibitors. These cells were maintained at 37° C. with 5% $CO_2$ in a tissue culture incubator with Dulbecco's modified Eagle medium (DMEM) medium containing 10% Fetal bovine serum (FBS) (ATCC, Manassas, VA), Penicillin 100 U/ml, Streptomycin 100 µg/ml, and 100 µg/ml Hygromysin B (Roche, Indianapolis, IN). Screening assays were performed in myoblasts (grown in medium containing 10% FBS) in duplicate 96 well plates at a cell concentration of $5 \times 10^4$ cells per well in 100 ul volume. Cells were pretreated with various concentrations (0.01 ug/ml to 10 ug/ml) of compound for 24 hr duration before stimulating with tumor necrosis factor-α (TNF-α) (10 ng/ml) for another 24 hrs. Prednisolone was included in every plate tested as a positive control. After the completion of incubation cells were washed twice with PBS and lysed with cell lysis buffer to measure luciferase activity (Promega Corp, Madison, WI) using Centro LB 960 luminometer (Berthold technologies, GmbH & Co, Bad Wildbad, Germany). Relative luminescence units with TNF-α stimulation in the absence of drugs were considered as 100% percent and data was represented as % inhibition relative to TNF-α induced NF-kB activation.

Some of the compounds disclosed herein were tested in the C2C12 skeletal muscle cell luciferase assay and exhibited ≥100% inhibition at concentrations of 0.01, 0.1, and 1 ug/mL; 80-100% inhibition at concentrations of 0.01, 0.1, 1, and 10 ug/mL; 60-80% inhibition at concentrations of 0.01, 0.1, and 1 ug/mL; 40-60% inhibition at concentrations of 1 and 10 ug/mL; and 20-40% inhibition at concentrations of 10 ug/mL.

Cell viability was assayed in duplicate plates by MTT (3-[4,5-dimethylthiazol-2-yl]-2,5-diphenyl tetrazolium bromide) (Sigma, Saint Louis, Missouri) as per manufacturer's protocols. Percent cell viability was calculated relative to untreated cells. There was not a significant decrease in cell viability (<80%) for any of compounds tested at any of the doses (0.01, 0.1, 1, and 10 ug/mL) tested.

Inhibition of NF-kB Nuclear Translocation

Inhibition of TNF-α induced NF-kB activation was confirmed by nuclear translocation immunofluorescence assay. C2C12 cells were grown on cover slips and treated with TNF-α and compound at optimal concentrations as described above. Cells were fixed with acetone and stained with a rabbit anti-NF-kB (p60) antibody/anti-rabbit Texas red (Santa Cruz Biotech, Inc, Santa Cruz, and CA) and counterstained with 4', 6-Diamidino-2-phenylindole HCl (DAPI) (Invitrogen, CA) to visualize the nuclei. Some of the compounds disclosed herein were tested in the nuclear translocation immunofluorescence assay and blocked TNF-α induced NF-kB nuclear translocation.

In Vivo Mdx Mouse Model of Dystrophy

Separate groups (n=12-14) of mdx mice were treated with prednisolone (5 mg/kg/day; per oral in feed), Example 1 (20 and 40 mg/kg/day; per oral in feed) and Example 2 (20 and 40 mg/kg/day; per oral in feed) for 3 months. All mice underwent 30 min biweekly treadmill exercise during the treatment duration to unmask the mild disease phenotype of mdx mouse model.

Effect on Body Weight (BM)

Prednisolone treated mice showed significantly lower body weight (P<0.05) than untreated mice at 33.8 weeks age. Mice treated with some of the compounds disclosed herein at 20 and 40 mg/kg/day dosages gained significantly more body weight and gastrocnemius muscle mass than untreated mice.

Effect on In Vivo Motor Coordination and Strength

Motor coordination and strength were assessed using Rota-rod (Ugo Basile, VA, Italy) testing. Briefly, mice were trained on the rota-rod for two days before collecting data. Each acclimatization session consisted of four training sessions, 2 per day and each session lasting 120 seconds at a speed of 5 rpm). Each trial consisted of placing the mice on the rod at 10 rpm for 60 seconds (stabilizing period) followed by an acceleration from 10 rpm to 40 rpm within the first 25 seconds until the animal fell from the rod or until 180 seconds are reached. If the animals fell during the stabilizing period, they were placed back on the rod to complete the session. The total testing time was 240 seconds (60 seconds stabilization time and 180 seconds test time). Each trial was performed twice a day (2 hour interval between sessions) for 3 consecutive days. The latency to fall (seconds) was recorded and all six scores were averaged per mouse. The average data was expressed as latency to fall (in seconds) for each group mice at 3 age groups. The ability of untreated mice to stay on the rod did not change significantly with time. Mice treated with some of the compounds disclosed herein at 20 and 40 mg/kg/day dosages showed increased latency to fall at 12, 24, or 36 weeks. In some instances, latency to fall was decreased or unchanged, increased by 0-10%, increased by 10-20%, increased by 20-30%, or increased by 30-40%.

Effect on In Vitro Force Contractions:

The distal tendon of the extensor digitorum longus (EDL) muscle was tied securely to the lever arm of a servomotor/force transducer (model 305B, Aurora Scientific, Richmond Hill, ON, Canada) and the proximal tendon to a tissue clamp. Muscles were stimulated between two platinum electrodes. With supramaximal stimulation of the muscle using single 0.2-ms square stimulation pulses for the EDL, muscle length was adjusted to the length ($L_o$) that resulted in maximal twitch force. With the muscle held at $L_o$ using stimulation frequencies of 30, 50, 80, 100, 120 and 150 Hz, the maximum isometric tetanic force force ($P_o$) developed during a 300 ms train of stimulation pulses was recorded for the EDL muscle. The muscle length was then measured with calipers and after removal of the muscle from the bath the mass of the muscle was determined. For each muscle, the optimum fiber length ($L_f$) was calculated by multiplying $L_o$ by a previously determined $L_f/L_o$ ratio of 0.45. Total muscle fiber cross-sectional area was determined by dividing the wet mass by the product of $L_f$ and the density of mammalian skeletal muscle (1.06 mg/mm$^3$). Maximum isometric specific force ($sP_o$) was determined by dividing $P_o$ by the total muscle fiber cross-sectional area. There was no statistically significant (P<0.05) difference in specific force between untreated and prednisolone groups. Mice treated with some of the compounds disclosed herein at 20 and 40 mg/kg/day dosages showed statistically significant (P<0.05) increased isometric specific force. In some instances, isometric specific force was decreased or unchanged, increased by 0-5%, increased by 5-10%, increased by 10-15%, or increased by 15-20%.

Histological Evaluations

Hematoxylin and Eosin staining of gastrocnemius muscle of untreated mdx mice show significant degeneration and inflammation. Skeletal muscle from Example 1- and Example 2-treated mice showed significant decrease in inflammation, degeneration, and increase in regenerating muscle fibers in comparison to untreated and prednisolone treated mdx mice. Continuous administration of prednisolone appeared to increase degeneration and decrease in regeneration of dystrophic skeletal muscle.

Glucocorticoid Receptor Binding Assay

To determine the receptor binding affinity of example compounds to the glucocorticoid receptor (GR), a ligand binding assay was performed using cDNA expression clones (Baculovirus) for human and mouse glucocorticoid receptor-alpha. Liver extracts containing different GR constructs were incubated with radiolabeled 3H-Dexamethsone (Amersham Pharmacia Biotech) and test compound in assay buffer (10 mM Tris-HCl, 1.5 mM EDTA, 10% glycerol, 1 mM dithiothreitol, and 20 mM sodium molybdate, pH 7.6). The amount of radioactivity was measured using a scintillation plate reader. Dexamethasone showed competitive binding with 3H-dexamethasone at micromolar concentrations. Some of the compounds disclosed herein were tested in the glucocorticoid receptor binding assay and found to have no significant (>75%) competitive binding to the glucocorticoid receptor at millimolar concentrations.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising between 10 to 200 mg of a compound having the structural formula

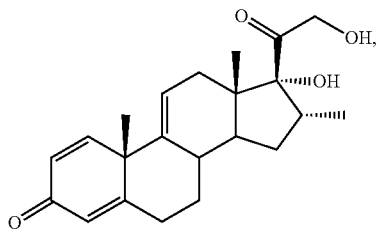 [SMILES: C[C@@H]1CC2C3CCC4=CC(=O)C=C[C@]4(C)C3=CC[C@]2(C)[C@@]1(O)C(=O)CO]

or a salt thereof,
wherein the pharmaceutical composition is formulated for oral administration and
wherein the compound is present in an amount effective to treat or reduce the symptoms of muscular dystrophy.

2. The pharmaceutical composition of claim 1, wherein the pharmaceutical composition is formulated as a tablet or capsule.

3. The pharmaceutical composition of claim 1, wherein the pharmaceutical composition is formulated as a solution or suspension.

4. The pharmaceutical composition of claim 1, wherein the pharmaceutical composition further comprises a flavoring agent.

5. The pharmaceutical composition of claim 1, wherein the muscular dystrophy is chosen from Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

6. The pharmaceutical composition of claim 5, wherein the muscular dystrophy is Duchenne muscular dystrophy.

7. A pharmaceutical composition comprising between 5 to 500 mg of a compound having the structural formula

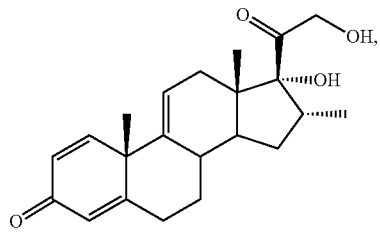 [SMILES: C[C@@H]1CC2C3CCC4=CC(=O)C=C[C@]4(C)C3=CC[C@]2(C)[C@@]1(O)C(=O)CO]

or a salt thereof,
wherein the pharmaceutical composition is formulated for oral administration and
wherein the compound is present in an amount effective to treat or reduce the symptoms of a muscular dystrophy chosen from Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

8. The pharmaceutical composition of claim 7, wherein the pharmaceutical composition is formulated as a tablet or capsule.

9. The pharmaceutical composition of claim 7, wherein the pharmaceutical composition is formulated as a solution or suspension.

10. The pharmaceutical composition of claim 7, wherein the pharmaceutical composition further comprises a flavoring agent.

11. The pharmaceutical composition of claim 7, wherein the therapeutically effective amount is between 10 mg to 200 mg of the compound.

12. The pharmaceutical composition of claim 7, wherein the muscular dystrophy is Duchenne muscular dystrophy.

* * * * *